(12) United States Patent
Scheller et al.

(10) Patent No.: US 10,772,676 B2
(45) Date of Patent: Sep. 15, 2020

(54) MICROSURGICAL BIPOLAR FORCEPS

(71) Applicant: Kogent Surgical, LLC, Chesterfield, MO (US)

(72) Inventors: Gregg D Scheller, Wildwood, MO (US); Jacob D Harris, St. Louis, MO (US)

(73) Assignee: KOGENT SURGICAL, LLC, Chesterfield, MO (US)

( * ) Notice: Subject to any disclaimer, the term of this patent is extended or adjusted under 35 U.S.C. 154(b) by 309 days.

(21) Appl. No.: 15/589,334

(22) Filed: May 8, 2017

(65) Prior Publication Data

US 2017/0340380 A1    Nov. 30, 2017

Related U.S. Application Data

(60) Provisional application No. 62/343,614, filed on May 31, 2016.

(51) Int. Cl.
*A61B 18/14* (2006.01)
*A61B 18/00* (2006.01)

(52) U.S. Cl.
CPC ...... *A61B 18/1445* (2013.01); *A61B 18/1492* (2013.01); *A61B 2018/00184* (2013.01);
(Continued)

(58) Field of Classification Search
CPC ............ A61B 18/1445; A61B 18/1492; A61B 2018/00184; A61B 2018/00321;
(Continued)

(56) References Cited

U.S. PATENT DOCUMENTS

| 3,100,489 | A | 8/1963 | Bagley |
| 4,567,890 | A | 2/1986 | Ohta et al. |

(Continued)

FOREIGN PATENT DOCUMENTS

EP    17099232 A2    11/2006

OTHER PUBLICATIONS

Sutter; "SuperGliss non-stick bipolar forceps" brochure—2012.
(Continued)

*Primary Examiner* — Daniel W Fowler
*Assistant Examiner* — Tigist S Demie

(57) ABSTRACT

A microsurgical bipolar forceps may include an actuation structure, a hypodermic tube, a first electrical conductor, and a second electrical conductor. The actuation structure may include an actuation structure distal end, an actuation structure proximal end, and a plurality of actuation limbs. The hypodermic tube may be disposed in the actuation structure. The first electrical conductor may be disposed in the hypodermic tube and the actuation structure wherein the first electrical conductor is electrically connected to a bipolar cord. The second electrical conductor may be disposed in the hypodermic tube and the actuation structure wherein the second electrical conductor is electrically connected to the bipolar cord. A compression of the actuation structure may be configured to decrease a distance between a first jaw of the first electrical conductor and a second jaw of the second electrical conductor.

20 Claims, 8 Drawing Sheets

(52) U.S. Cl.
CPC ........... *A61B 2018/00321* (2013.01); *A61B 2018/00339* (2013.01); *A61B 2018/00351* (2013.01); *A61B 2018/00565* (2013.01); *A61B 2218/002* (2013.01)

(58) Field of Classification Search
CPC .......... A61B 2018/00339; A61B 2018/00351; A61B 2018/00565; A61B 2218/002
See application file for complete search history.

(56) References Cited

U.S. PATENT DOCUMENTS

| | | | |
|---|---|---|---|
| 5,647,871 A | 7/1997 | Levine et al. | |
| 5,674,220 A | 10/1997 | Fox et al. | |
| 6,050,996 A | 4/2000 | Schmaltz et al. | |
| 6,228,084 B1 | 5/2001 | Kirwan, Jr. | |
| 6,231,574 B1 | 5/2001 | Posthuma | |
| 6,231,591 B1* | 5/2001 | Desai | A61B 8/0841 604/8 |
| 6,293,946 B1 | 9/2001 | Thorne | |
| 6,482,205 B1 | 11/2002 | Bonnet | |
| 6,679,881 B1 | 1/2004 | Bybee | |
| 6,749,610 B2 | 6/2004 | Kirwan, Jr. et al. | |
| 6,767,348 B2 | 7/2004 | Nakada et al. | |
| 6,860,882 B2 | 3/2005 | Battles et al. | |
| 6,863,669 B2 | 3/2005 | Spitzer | |
| 7,122,035 B2 | 10/2006 | Canady | |
| 7,150,097 B2 | 12/2006 | Sremcich et al. | |
| D559,984 S | 1/2008 | Scheller | |
| 7,402,754 B2 | 7/2008 | Kirwan, Jr. et al. | |
| 7,621,911 B2 | 11/2009 | Ariola, Jr. | |
| 7,736,361 B2 | 6/2010 | Palanker et al. | |
| 7,867,230 B2 | 1/2011 | Asahara et al. | |
| 7,963,965 B2 | 6/2011 | Buysse et al. | |
| 8,048,107 B2 | 11/2011 | Chen | |
| 8,083,735 B2 | 12/2011 | Morris | |
| 8,108,994 B2 | 2/2012 | Ariola, Jr. et al. | |
| 8,192,433 B2 | 6/2012 | Johnson et al. | |
| 8,211,105 B2 | 7/2012 | Buysee et al. | |
| 8,241,278 B2 | 8/2012 | Sartor | |
| 8,469,956 B2 | 6/2013 | McKenna et al. | |
| D707,816 S | 6/2014 | LaMontagne et al. | |
| D707,817 S | 6/2014 | Schallert | |
| 9,149,389 B2 | 10/2015 | Scheller et al. | |
| 2003/0129382 A1 | 7/2003 | Treat | |
| 2003/0181909 A1 | 9/2003 | Kirwan, Jr. | |
| 2004/0034349 A1 | 2/2004 | Kirwan, Jr. et al. | |
| 2005/0107784 A1 | 5/2005 | Moses et al. | |
| 2006/0004356 A1 | 1/2006 | Bilski et al. | |
| 2006/0135956 A1* | 6/2006 | Sampson | A61B 17/42 606/41 |
| 2006/0217706 A1 | 9/2006 | Lau et al. | |
| 2006/0217709 A1 | 9/2006 | Couture et al. | |
| 2006/0235466 A1 | 10/2006 | McGarity et al. | |
| 2008/0200914 A1 | 8/2008 | Hanlon et al. | |
| 2011/0054461 A1 | 3/2011 | Dickhans | |
| 2012/0004653 A1 | 1/2012 | Butsch | |
| 2012/0310237 A1 | 12/2012 | Swanson | |
| 2013/0066317 A1 | 3/2013 | Evans et al. | |
| 2013/0226177 A1 | 8/2013 | Brandt et al. | |
| 2014/0018788 A1 | 1/2014 | Engleman et al. | |
| 2014/0128909 A1 | 5/2014 | Scheller et al. | |
| 2014/0142603 A1 | 5/2014 | Scheller et al. | |
| 2014/0194870 A1 | 7/2014 | Hanlon et al. | |
| 2014/0200576 A1 | 7/2014 | Scheller et al. | |
| 2014/0276804 A1 | 9/2014 | Batchelor | |

OTHER PUBLICATIONS

Stingray Surgical Products, Inc. brochure—2010.
Olsen Medical; "Single Use Bipolar Forceps" brochure—2008.
Codman; Bipolar brochure—2003.
Micromed brochure—2012.
Aesculap brochure, May 12, 2012.
Sutter; "Bipolar Forceps" brochure—2012.
Manuel Dujovny et al., Bipolar Jeweler's Forceps With Automatic Irrigation, for Coagulation in Microsurgery, Plastic and Reconstructive Surgery, 585-587, Nov. 1975.
Ananth K. Vellimana et al., Current Technological Advances of Bipolar Coagulation, Operative Neurosurgery, No. 1, vol. 64, 11-19, Mar. 2009.
Ebonia W. Elliott-Lewis et al., Evaluation of New Bipolar Coagulation Forceps in a Thermal Damage Assessment, Operative Neurosurgery, No. 6, vol. 65, 1182-1187, Dec. 2009.
Manuel Dujovny et al., Bipolar Coagulation in Neurosurgery, Surg. Neurol. 1998; 49:328-32.
Leonard I. Malis, Electrosurgery and Bipolar Technology, Operative Neurosurgery, No. 1, vol. 58, 1-12, Feb. 2006.
Ebonia W. Elliott-Lewis et al., Thermal Damage Assessment of Novel Bipolar Forceps in a Sheep Model of Spinal Surgery, Neurosurgery 67:166-172, 2010.
Soring Product Catalog, Sep. 2011.
510 (k) Summary of Safety and Effectiveness, K110924, Dec. 7, 2011.
Aesculap Non-Stick Bipolar brochure—2016.

\* cited by examiner

MICROSURGICAL BIPOLAR FORCEPS

CROSS-REFERENCE TO RELATED APPLICATIONS

This Application claims the benefit of U.S. Provisional Application No. 62/343,614, filed May 31, 2016.

FIELD OF THE INVENTION

The present disclosure relates to a surgical instrument, and, more particularly, to an electrosurgical instrument.

BACKGROUND OF THE INVENTION

A variety of complete surgical procedures and portions of surgical procedures may be performed with bipolar forceps, e.g., bipolar forceps are commonly used in dermatological, gynecological, cardiac, plastic, ocular, spinal, maxillofacial, orthopedic, urological, and general surgical procedures. Bipolar forceps are also used in neurosurgical procedures; however, the use of bipolar forceps in neurosurgical procedures presents unique risks to patients if the surgeon is unable to both visually and tactilely confirm that an electrosurgical procedure is being performed as intended. Accordingly, there is a need for a bipolar forceps that allows a surgeon to both visually and tactilely confirm that an electrosurgical procedure is being performed as intended. After an electrosurgical procedure is performed as intended, cauterized tissue may adhere to the electrodes of the bipolar forceps which must be removed before another electrosurgical procedure may be performed effectively. Accordingly, there is a need for a bipolar forceps that reduces adherence of cauterized tissue to electrodes. Some surgical procedures require cauterization of extremely small tissues, e.g., some surgical procedures require access to extremely small tissues disposed several inches below a surface of a surgical site. Accordingly, there is a need for a microsurgical bipolar forceps.

BRIEF SUMMARY OF THE INVENTION

A microsurgical bipolar forceps is presented. In one or more embodiments, a microsurgical bipolar forceps may comprise an actuation structure, a hypodermic tube, a first electrical conductor, and a second electrical conductor. Illustratively, the actuation structure may comprise an actuation structure distal end, an actuation structure proximal end, and a plurality of actuation limbs. In one or more embodiments, the hypodermic tube may be disposed in the actuation structure. Illustratively, the first electrical conductor may be disposed in the hypodermic tube and the actuation structure wherein the first electrical conductor is electrically connected to a bipolar cord. In one or more embodiments, the second electrical conductor may be disposed in the hypodermic tube and the actuation structure wherein the second electrical conductor is electrically connected to the bipolar cord. Illustratively, a compression of the actuation structure may be configured to decrease a distance between a first jaw of the first electrical conductor and a second jaw of the second electrical conductor. In one or more embodiments, a decompression of the actuation structure may be configured to increase the distance between the first jaw of the first electrical conductor and the second jaw of the second electrical conductor.

BRIEF DESCRIPTION OF THE DRAWINGS

The above and further advantages of the present invention may be better understood by referring to the following description in conjunction with the accompanying drawings in which like reference numerals indicate identical or functionally similar elements.

DETAILED DESCRIPTION OF AN ILLUSTRATIVE EMBODIMENT

Figure 1A:
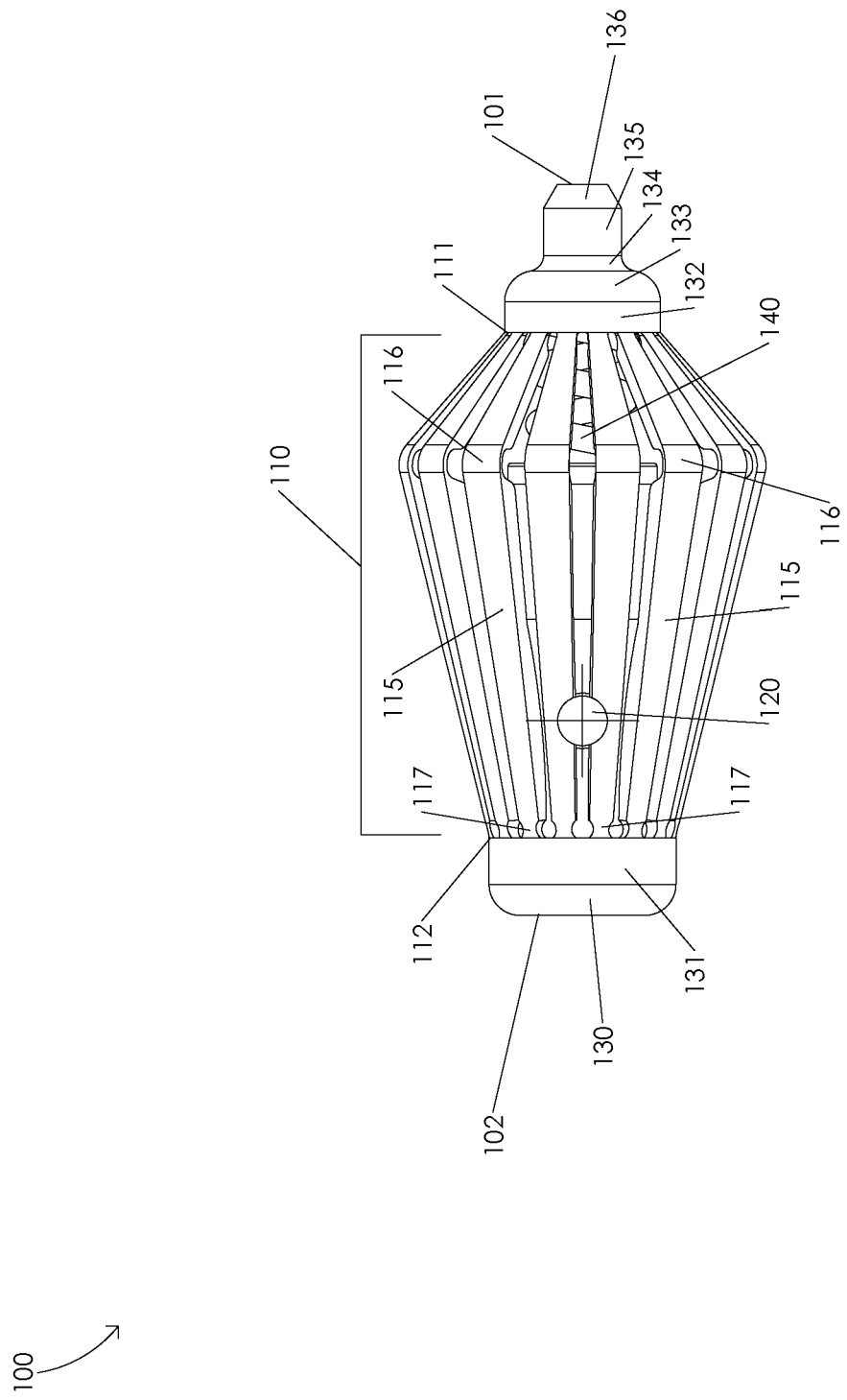
FIGS. 1A and 1B are schematic diagrams illustrating a handle.
Figure 1B:
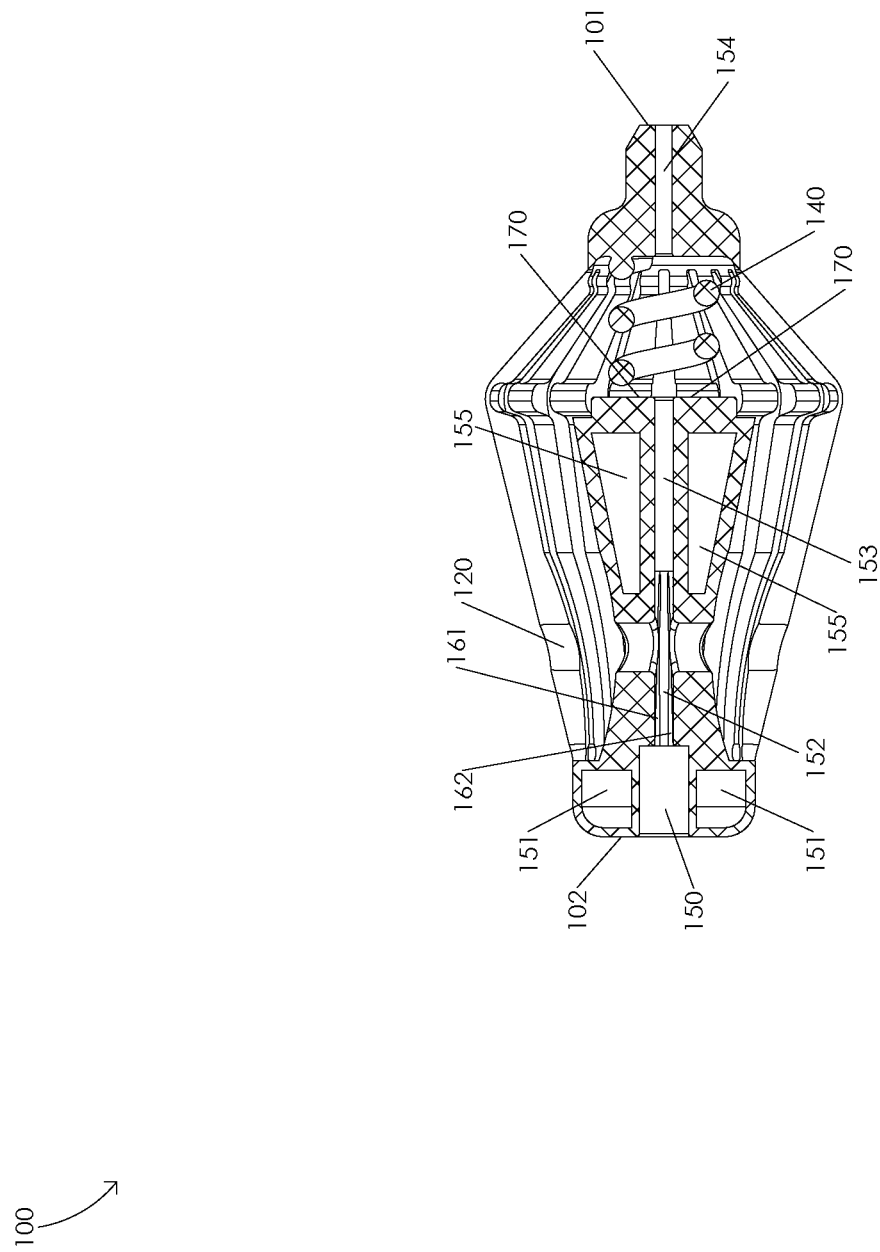

FIGS. 1A and 1B are schematic diagrams illustrating a handle 100. FIG. 1A is a schematic diagram illustrating a side view of a handle 100. In one or more embodiments, a handle 100 may comprise a handle distal end 101 and a handle proximal end 102. Illustratively, handle 100 may comprise an actuation structure 110 having an actuation structure distal end 111 and an actuation structure proximal end 112. In one or more embodiments, handle 100 may comprise a proximal ring 131 and a distal ring 132, e.g., handle 100 may comprise a proximal ring 131 disposed adjacent to actuation structure proximal end 112 and handle 100 may comprise a distal ring 132 disposed adjacent to actuation structure distal end 111. For example, proximal ring 131 may abut actuation structure proximal end 112 and distal ring 132 may abut actuation structure distal end 111. Illustratively, handle 100 may comprise a handle base 130, e.g., handle 100 may comprise a handle base 130 disposed adjacent to proximal ring 131. For example, handle base 130 may abut proximal ring 131. In one or more embodiments, handle 100 may comprise a first nosecone fillet 133, e.g., handle 100 may comprise a first nosecone fillet 133 disposed adjacent to distal ring 132. For example, first nosecone fillet 133 may abut distal ring 132. Illustratively, handle 100 may comprise a second nosecone fillet 134, e.g., handle 100 may comprise a second nosecone fillet 134 disposed adjacent to first nosecone fillet 133. For example, second nosecone fillet 134 may abut first nosecone fillet 133. In one or more embodiments, handle 100 may comprise a nosecone base 135, e.g., handle 100 may comprise a nosecone base 135 disposed adjacent to second nosecone fillet 134. For example, nosecone base 135 may abut second nosecone fillet 134. Illustratively, handle 100 may comprise a nosecone taper 136, e.g., handle 100 may comprise a nosecone taper 136 disposed adjacent to nosecone base 135. For example, nosecone taper 136 may abut nosecone base 135.

In one or more embodiments, actuation structure 110 may comprise a plurality of actuation limbs 115. Illustratively, each actuation limb 115 may comprise an expanding joint 116 and a hinge 117. In one or more embodiments, actuation structure 110 may comprise a shape memory material configured to project actuation structure distal end 111 a first distance from actuation structure proximal end 112, e.g., when actuation structure 110 is fully decompressed. Illustratively, actuation structure 110 may comprise a shape memory material configured to project actuation structure distal end 111 a second distance from actuation structure proximal end 112, e.g., when actuation structure 110 is fully compressed. In one or more embodiments, the second distance from actuation structure proximal end 112 may be greater than the first distance from actuation structure proximal end 112. Actuation structure 110 may be manufactured from any suitable material, e.g., polymers, metals, metal alloys, etc., or from any combination of suitable materials.

Illustratively, actuation structure 110 may be compressed by an application of a compressive force to actuation structure 110. In one or more embodiments, actuation structure 110 may be compressed by an application of one or more compressive forces located at one or more locations around an outer perimeter of actuation structure 110. Illustratively, the one or more locations may comprise any of a plurality of locations around the outer perimeter of actuation structure 110. For example, a surgeon may compress actuation structure 110 by squeezing actuation structure 110. Illustratively, the surgeon may compress actuation structure 110 by squeezing actuation structure 110 at any particular location of a plurality of locations around an outer perimeter of actuation structure 110. For example, a surgeon may rotate handle 100 and compress actuation structure 110 from any rotational position of a plurality of rotational positions of handle 100.

In one or more embodiments, actuation structure 110 may be compressed by an application of a compressive force to any one or more of the plurality of actuation limbs 115. Illustratively, each actuation limb 115 may be configured to actuate independently. In one or more embodiments, each actuation limb 115 may be connected to one or more of the plurality of actuation limbs 115 wherein an actuation of a particular actuation limb 115 may be configured to actuate every actuation limb 115 of the plurality of actuation limbs 115. Illustratively, one or more actuation limbs 115 may be configured to actuate in pairs or groups. For example, an actuation of a first actuation limb 115 may be configured to actuate a second actuation limb 115. In one or more embodiments, a compression of actuation structure 110, e.g., due to an application of a compressive force to a particular actuation limb 115, may be configured to actuate the particular actuation limb 115. Illustratively, an actuation of the particular actuation limb 115 may be configured to actuate every actuation limb 115 of the plurality of actuation limbs 115.

In one or more embodiments, an application of a compressive force to a particular actuation limb 115 may be configured to extend at least one expanding joint 116 of the particular actuation limb 115, e.g., an application of a compressive force to a particular actuation limb 115 may be configured to expand at least one expanding joint 116 of the particular actuation limb 115. Illustratively, a particular actuation limb 115 may be configured to extend a first distance from handle base 110. An extension of an expanding joint 116 of the particular actuation limb 115, e.g., due to an application of a compressive force to the particular actuation limb 115, may be configured to extend the particular actuation limb 115 a second distance from handle base 110. Illustratively, the second distance from handle base 110 may be greater than the first distance from handle base 110. In one or more embodiments, distal ring 132 may be configured to extend a first distance from proximal ring 131 when actuation structure 110 is fully decompressed. Illustratively, a compression of actuation structure 110 may be configured to extend distal ring 132 a second distance from proximal ring 131. In one or more embodiments, the second distance from proximal ring 131 may be greater than the first distance from proximal ring 131.

FIG. 1B is a schematic diagram illustrating a cross-sectional view in a sagittal plane of a handle 100. In one or more embodiments, a handle 100 may comprise a wire lock housing 120, a spring 140, and an end plug housing 150. Illustratively, wire lock housing 120 may be disposed between spring 140 and end plug housing 150. Illustratively, handle 100 may comprise a proximal void 151 and a distal void 155. In one or more embodiments, proximal void 151 and distal void 155 may be configured to reduce a mass of handle 100. Illustratively, handle 100 may comprise a proximal inner lumen 152, a distal inner lumen 153, and a hypodermic tube housing 154. In one or more embodiments, distal inner lumen 153 may be disposed between proximal inner lumen 152 and hypodermic tube housing 154. Illustratively, handle 100 may comprise a ring interface 170. In one or more embodiments, handle 100 may comprise a first irrigation fluid channel 161 and a second irrigation fluid channel 162. Illustratively, first irrigation fluid channel 161 and second irrigation fluid channel 162 may be configured to direct a flow of irrigation fluid within handle 100. In one or more embodiments, proximal inner lumen 152 may be disposed between first irrigation fluid channel 161 and second irrigation fluid channel 162. Handle 100 may be manufactured from any suitable material, e.g., polymers, metals, metal alloys, etc., or from any combination of suitable materials.

In one or more embodiments, handle 100 may be manufactured from a material configured to deform if handle 100 is sterilized in a medical autoclave, e.g., handle 100 may be manufactured from a material configured to permanently deform if handle 100 is sterilized in a medical autoclave. Illustratively, handle 100 may be manufactured from a material having a melting point below a temperature parameter for a steam sterilization cycle, e.g., handle 100 may be manufactured from a material having a melting point below a temperature parameter for a gravity-displacement steam sterilization cycle, a dynamic-air-removal steam sterilization cycle, etc. In one or more embodiments, handle 100 may be manufactured from a material having a melting point below 140.0 degrees Fahrenheit. Illustratively, handle 100 may be manufactured from a material having a melting point in a range of 158.0 to 212.0 degrees Fahrenheit, e.g., handle 100 may be manufactured from a material having a melting point of 160.0 degrees Fahrenheit. In one or more embodiments, handle 100 may be manufactured from a material having a melting point of less than 158.0 degrees Fahrenheit or greater than 212.0 degrees Fahrenheit. In one or more embodiments, handle 100 may be manufactured from a material having a melting point below 250.0 degrees Fahrenheit. Illustratively, handle 100 may be manufactured from a material having a melting point below 270.0 degrees Fahrenheit. In one or more embodiments, handle 100 may be manufactured from a material having a melting point below 275.0 degrees Fahrenheit.

Illustratively, handle 100 may be manufactured from a material configured to temporarily deform if handle 100 is sterilized in a medical autoclave, e.g., handle 100 may be manufactured from a material configured to absorb water in a medical autoclave. In one or more embodiments, an absorption of water may be configured to deform handle 100, e.g., an absorption of water may be configured to cause handle 100 to expand. Illustratively, handle 100 may be manufactured from a porous material configured to facilitate a deformation of handle 100 if handle 100 is sterilized in a medical autoclave. In one or more embodiments, handle 100 may be manufactured with one or more cavities configured to facilitate a deformation of handle 100 if handle 100 is sterilized in a medical autoclave. Illustratively, handle 100 may be manufactured from any suitable material, e.g., polymers, metals, metal alloys, etc., or from any combination of suitable materials. In one or more embodiments, handle 100 may be manufactured by a 3D printing process.

For example, handle 100 may be manufactured by selective laser sintering, selective heat sintering, selective laser melting, electron-beam melting, direct metal laser sintering, electron beam freeform fabrication, etc. Illustratively, handle 100 may be manufactured by injection molding.

In one or more embodiments, handle 100 may be manufactured from poly(acrylamide), poly(acrylic acid), poly(adipic anhydride), poly(7-aminoenanthic acid), poly(12-aminolauric acid), poly(11-aminoundecanoic acid), poly(azelaic anhydride), poly[1,3-butadiene(1,4-)-alt-methacrylonitrile], poly[1,3-butadiene(1,4-)-alt-methyl methacrylate], poly(butadiene oxide), poly(caprylaldehyde), poly(1,4-cyclohexylenedimethylene azelate), poly(1,4-cyclohexylenedimethylene dodecanedioate), poly(1,4-cyclohexylenedimethylene glutarate), poly(1,4-cyclohexylenedimethylene p-phenylenediacetate), poly(1,4-cyclohexylenedimethylene pimelate), poly(1,4-cyclohexylenedimethylene sebacate), poly(1,4-cyclohexylenedimethylene suberate), poly(cyclohexylidenethiohexamethylene sulfide), poly(cyclopropylenedimethylene piperazinediurethane), poly(cyclopropylidenedimethylene oxide), poly(decamethylene), poly(decamethylene carbonate), poly[(decamethylenedioxy)-dihexamethylene oxide], poly(decamethylene disulfide), poly(decamethylenedithioethylene disulfide), poly(decamethylenedithiohexamethylene disulfide), poly(decamethylene dithioladipate), poly(decamethylenedithiotetramethylene disulfide), poly(decamethylene pimelate), poly(decamethylene fumaramide), poly(decamethylene glutaramide), poly(decamethylene isophthalate), poly(decamethylene malonate), poly(decamethylene oxydiacetate), poly(decamethyleneoxymethylene oxide), poly(decamethylene succinate), poly(decamethylene sulfide), poly(decamethylene thiodivalerate), poly(decamethylenethiohexamethylene sulfide), poly(divinylbenzal), poly(dodecamethylene), poly(dodecanedioic anhydride), poly(eicosamethylene adipate), poly(eicosamethylene azelate), poly(eicosamethylene glutarate), poly(eicosamethylene isophthalate), poly(eicosamethylene malonate), poly(eicosamethylene oxalate), poly(eicosamethylene oxydiacetate), poly(eicosamethylene phthalate), poly(eicosamethylene pimelate), poly(eicosamethylene sebacate), poly(eicosamethylene suberate), poly(eicosamethylene succinate), poly(eicosamethylene thiodivalerate), poly[ethylene p-(carboxyphenoxy)-butyrate], poly[ethylene p-(carboxyphenoxy)caproate], poly[ethylene p-(carboxyphenoxy)-heptanoate], poly[ethylene p(carboxyphenoxy)-undecanoate], poly[ethylene p-(carboxyphenoxy)-valerate], poly(ethylene 2,2'-dibenzoate), poly[(ethylenedioxy)-diethylene 2,2'-dibenzoate], poly(ethylene 2,2'-dibenzoate), poly[(ethylenedioxy)-diethylene 3,3'-dibenzoate], poly[(ethylenedioxy)-diethylene isophthalate], poly[(ethylenedioxy)-diethylene sebacate], poly[(ethylenedioxy)-diethylene thiodivalerate], poly(ethylene disiloxanylenedipropionamide), poly[(ethylenedithio)-diacetic anhydride], poly[(ethylenedithio)-dipropionic anhydride], poly(ethylene dithionisophthalate), poly(ethelene dithiotetra-methylene disulfide), poly(ethylene fumaramide), poly(ethylene glutarate), poly(ethylene 2,4-hexadienediamide), poly(ethylene phthalate), poly(ethylene sulfonyldivalerate), poly(ethylene terephthalate), poly(heptamethylene), poly(hexamethylene azelate), poly(hexamethylene carbonate), poly[hexamethylene p-(carboxyphenoxy)-acetate], poly[hexamethylene p-(carboxyphenoxy)-caproate], poly[hexamethylene p-(carboxyphenoxy)-undecanoate], poly[hexamethylene p-(carboxyphenoxy)-valerate], poly(hexamethylene isophthalate), poly[hexamethylene (methylene-2,5-tetrahydrofuran)-dicarboxamide], poly(hexamethylene octadecanediamide), poly(hexamethylene oxydiacetate), poly(hexamethylene 4,4'-oxydibenzoate), poly(hexamethylene pimelate), poly(hexamethylene succinate), poly(hexamethylene thiodivalerate), poly(hexamethylenethiooentamethylene sulfide), poly(hexamethylenethiotetramethylene sulfide), poly(hexenamer), etc. Illustratively, handle 100 may be manufactured from any substituted polymers of poly(acrylamide), poly(acrylic acid), poly(adipic anhydride), poly(7-aminoenanthic acid), poly(12-aminolauric acid), poly(11-aminoundecanoic acid), poly(azelaic anhydride), poly[1,3-butadiene(1,4-)-alt-methacrylonitrile], poly[1,3-butadiene(1,4-)-alt-methyl methacrylate], poly(butadiene oxide), poly(caprylaldehyde), poly(1,4-cyclohexylenedimethylene azelate), poly(1,4-cyclohexylenedimethylene dodecanedioate), poly(1,4-cyclohexylenedimethylene glutarate), poly(1,4-cyclohexylenedimethylene p-phenylenediacetate), poly(1,4-cyclohexylenedimethylene pimelate), poly(1,4-cyclohexylenedimethylene sebacate), poly(1,4-cyclohexylenedimethylene suberate), poly(cyclohexylidenethiohexamethylene sulfide), poly(cyclopropylenedimethylene piperazinediurethane), poly(cyclopropylidenedimethylene oxide), poly(decamethylene), poly(decamethylene carbonate), poly[(decamethylenedioxy)-dihexamethylene oxide], poly(decamethylene disulfide), poly(decamethylenedithioethylene disulfide), poly(decamethylenedithiohexamethylene disulfide), poly(decamethylene dithioladipate), poly(decamethylenedithiotetramethylene disulfide), poly(decamethylene pimelate), poly(decamethylene fumaramide), poly(decamethylene glutaramide), poly(decamethylene isophthalate), poly(decamethylene malonate), poly(decamethylene oxydiacetate), poly(decamethyleneoxymethylene oxide), poly(decamethylene succinate), poly(decamethylene sulfide), poly(decamethylene thiodivalerate), poly(decamethylenethiohexamethylene sulfide), poly(divinylbenzal), poly(dodecamethylene), poly(dodecanedioic anhydride), poly(eicosamethylene adipate), poly(eicosamethylene azelate), poly(eicosamethylene glutarate), poly(eicosamethylene isophthalate), poly(eicosamethylene malonate), poly(eicosamethylene oxalate), poly(eicosamethylene oxydiacetate), poly(eicosamethylene phthalate), poly(eicosamethylene pimelate), poly(eicosamethylene sebacate), poly(eicosamethylene suberate), poly(eicosamethylene succinate), poly(eicosamethylene thiodivalerate), poly[ethylene p-(carboxyphenoxy)-butyrate], poly[ethylene p-(carboxyphenoxy)-caproate], poly[ethylene p-(carboxyphenoxy)-heptanoate], poly[ethylene p-(carboxyphenoxy)-undecanoate], poly[ethylene p-(carboxyphenoxy)-valerate], poly(ethylene 2,2'-dibenzoate), poly[(ethylenedioxy)-diethylene 2,2'-dibenzoate], poly(ethylene 2,2'-dibenzoate), poly[(ethylenedioxy)-diethylene 3,3'-dibenzoate], poly[(ethylenedioxy)-diethylene isophthalate], poly[(ethylenedioxy)-diethylene sebacate], poly[(ethylenedioxy)-diethylene thiodivalerate], poly(ethylene di siloxanylenedi-propionami de), poly[(ethylenedithio)-diacetic anhydride], poly[(ethylenedithio)-dipropionic anhydride], poly(ethylene dithionisophthalate), poly(ethelene dithiotetra-methylene disulfide), poly(ethylene fumaramide), poly(ethylene glutarate), poly(ethylene 2,4-hexadienediamide), poly(ethylene phthalate), poly(ethylene sulfonyldivalerate), poly(ethylene terephthalate), poly(heptamethylene), poly(hexamethylene azelate), poly(hexamethylene carbonate), poly[hexamethylene p-(carboxyphenoxy)-acetate], poly[hexamethylene p-(carboxyphenoxy)-caproate], poly[hexamethylene p-(carboxyphenoxy)-undecanoate], poly[hexamethylene p-(carboxyphenoxy)-valerate], poly(hexamethylene isophthalate), poly[hexamethylene (methylene-2,5-tetrahydrofuran)-dicarboxamide], poly(hexamethylene octadecanediamide), poly(hexamethylene oxydiacetate), poly(hexamethylene 4,4'-oxydibenzoate), poly(hexamethylene pimelate), poly(hexamethylene succinate), poly(hexamethylene thiodivalerate), poly(hexamethylenethiooentamethylene sulfide), poly(hexamethylenethiotetramethylene sulfide), poly(hexenamer), etc.

Figure 2:
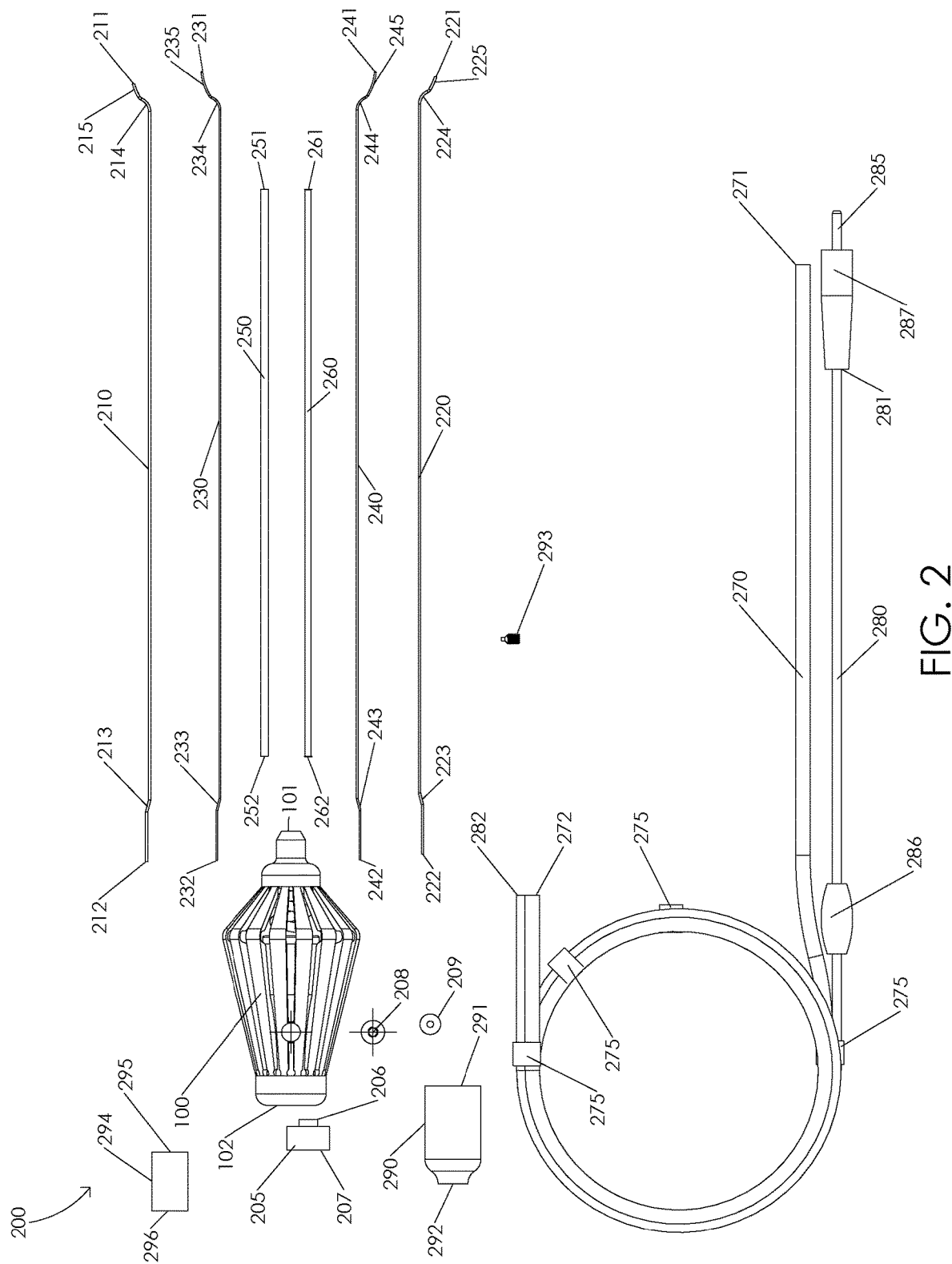
FIG. 2 is a schematic diagram illustrating an exploded view of a microsurgical bipolar forceps assembly.

FIG. 2 is a schematic diagram illustrating an exploded view of a microsurgical bipolar forceps assembly 200. In one or more embodiments, a microsurgical bipolar forceps assembly 200 may comprise a handle 100, a hypodermic tube 250, a first electrical conductor 230, a second electrical conductor 240, an irrigation tube 270, and a bipolar cord 280. Illustratively, hypodermic tube 250 may comprise a hypodermic tube distal end 251 and a hypodermic tube proximal end 252. In one or more embodiments, hypodermic tube 250 may have dimensions configured for performing microsurgical procedures, e.g., hypodermic tube 250 may have an outer diameter of less than 0.070 inches. Illustratively, hypodermic tube 250 may have an outer diameter in a range of 0.0142 to 0.085 inches, e.g., hypodermic tube 250 may have an outer diameter of 0.065 inches. In one or more embodiments, hypodermic tube 250 may have an outer diameter of less than 0.0142 inches or greater than 0.085 inches. Illustratively, hypodermic tube 250 may have an inner diameter in a range of 0.010 to 0.080 inches, e.g., hypodermic tube 250 may have an inner diameter of 0.0535 inches. In one or more embodiments, hypodermic tube 250 may have an inner diameter of less than 0.010 inches or greater than 0.080 inches. Illustratively, hypodermic tube 250 may have a length configured to extend more than halfway across a human head. In one or more embodiments, hypodermic tube 250 may have a length in a range of 3.85 to 6.25 inches, e.g., hypodermic tube 250 may have a length of 4.85 inches. Illustratively, hypodermic tube 250 may have a length of less than 3.85 inches or greater than 6.25 inches. In one or more embodiments, hypodermic tube 250 may be manufactured from any suitable material, e.g., polymers, metals, metal alloys, etc., or from any combination of suitable materials. Illustratively, hypodermic tube 250 may be manufactured from stainless steel, e.g., e.g., hypodermic tube 250 may be manufactured from Type 301 stainless steel, Type 302 stainless steel, Type 303 stainless steel, Type 304 stainless steel, Type 304L stainless steel, Type 304LN stainless steel, Type 310 stainless steel, Type 316 stainless steel, Type 316L stainless steel, Type 316Ti stainless steel, Type 321 stainless steel, Type 430 stainless steel, Type 440 stainless steel, Type 17-7 stainless steel, etc. Illustratively, hypodermic tube 250 may be manufactured from nitinol. In one or more embodiments, hypodermic tube 250 may be manufactured from aluminum, e.g., hypodermic tube 250 may be manufactured from an aluminum alloy. Illustratively, hypodermic tube 250 may be manufactured from a 6061 aluminum alloy, a 6061-T4 aluminum alloy, a 6061-T6 aluminum alloy, a 6063 aluminum alloy, a 6063 aluminum alloy, etc. In one or more embodiments, hypodermic tube 250 may be manufactured from titanium, e.g., hypodermic tube 250 may be manufactured from a titanium alloy. Illustratively, hypodermic tube 250 may be manufactured from a Grade 5 titanium alloy, a Grade 6 titanium alloy, a Grade 7H titanium alloy, a Grade 9 titanium alloy, a Grade 11 titanium alloy, a Grade 12 titanium alloy, a Grade 16 titanium alloy, a Grade 17 titanium alloy, a Grade 18 titanium alloy, etc.

In one or more embodiments, first electrical conductor 230 may comprise a first electrical conductor distal end 231, a first electrical conductor proximal end 232, a first electrical conductor posterior offset 233, a first ramp 234, and a first jaw 235. Illustratively, second electrical conductor 240 may comprise a second electrical conductor distal end 241, a second electrical conductor proximal end 242, a second electrical conductor posterior offset 243, a second ramp 244, and a second jaw 245. In one or more embodiments, irrigation tube 270 may comprise an irrigation tube distal end 271 and an irrigation tube proximal end 272. Illustratively, bipolar cord 280 may comprise a bipolar cord distal end 281 and a bipolar cord proximal end 282. In one or more embodiments, microsurgical bipolar forceps assembly 200 may comprise one or more fasteners 275 configured to attach irrigation tube 270 and bipolar cord 280. Illustratively, microsurgical bipolar forceps assembly 200 may comprise one or more bipolar conductors 285, a bipolar cord indicator 286, and an electrosurgical generator interface 287.

In one or more embodiments, microsurgical bipolar forceps assembly 200 may comprise an end plug 205, an outer sleeve 290, and an inner sleeve 294. Illustratively, end plug 205 may comprise an end plug distal end 206 and an end plug proximal end 207. In one or more embodiments, outer sleeve 290 may comprise an outer sleeve distal end 291 and an outer sleeve proximal end 292. Illustratively, inner sleeve 294 may comprise an inner sleeve distal end 295 and an inner sleeve proximal end 296. In one or more embodiments, microsurgical bipolar forceps assembly 200 may comprise a wire lock 208, a ring 209, and a setscrew 293. Illustratively, microsurgical bipolar forceps assembly 200 may comprise an electrical insulator tube 260, a first electrical insulator sleeve 210, and a second electrical insulator sleeve 220.

In one or more embodiments, electrical insulator tube 260 may comprise an electrical insulator tube distal end 261 and an electrical insulator tube proximal end 262. Illustratively, electrical insulator tube 260 may have dimensions configured to perform microsurgical procedures, e.g., electrical insulator tube 260 may have an outer diameter that is less than an inner diameter of hypodermic tube 250. In one or more embodiments, electrical insulator tube 260 may have an outer diameter in a range of 0.040 to 0.060 inches, e.g., electrical insulator tube 260 may have an outer diameter of 0.052 inches. Illustratively, electrical insulator tube 260 may have an outer diameter of less than 0.040 inches or greater than 0.060 inches. In one or more embodiments, electrical insulator tube 260 may have an inner diameter in a range of 0.040 to 0.060 inches, e.g., electrical insulator tube 260 may have an inner diameter of 0.052 inches. Illustratively, electrical insulator tube 260 may have an inner diameter of less than 0.040 inches or greater than 0.060 inches. In one or more embodiments, electrical insulator tube 260 may have a dry coefficient of friction in a range of 0.3 to 0.7, e.g., electrical insulator tube 260 may have a dry coefficient of friction of 0.5. Illustratively, electrical insulator tube 260 may have a dry coefficient of friction of less than 0.3 or greater than 0.7.

In one or more embodiments, electrical insulator tube 260 may be configured to prevent an electrical connection between a portion of hypodermic tube 250 and a portion of first electrical conductor 230, e.g., electrical insulator tube 260 may be configured to prevent an electrical current from flowing between a portion of hypodermic tube 250 and a portion of first electrical conductor 230. Illustratively, electrical insulator tube 260 may be configured to prevent an electrical connection between a portion of hypodermic tube 250 and a portion of second electrical conductor 240, e.g., electrical insulator tube 260 may be configured to prevent an electrical current from flowing between a portion of hypodermic tube 250 and a portion of second electrical conductor 240. In one or more embodiments, electrical insulator tube 260 may be manufactured from any suitable material, e.g., polymers, metals, metal alloys, etc., or from any combination of suitable materials. Illustratively, electrical insulator tube 260 may be manufactured from a material having a dielectric strength in a range of 3500 to 4500 volts per mil, e.g., electrical insulator tube 260 may be manufactured from a material having a dielectric strength of 4000 volts per mil. In one or more embodiments, electrical insulator tube 260 may be manufactured from a material having a dielectric strength of less than 3500 volts per mil or greater than 4500 volts per mil. Illustratively, electrical insulator tube 260 may be manufactured from a material having a thermal conductivity in a range of 0.25 to 0.60 watts per meter kelvin, e.g., electrical insulator tube 260 may be manufactured from a material having a thermal conductivity of 0.47 watts per meter kelvin. In one or more embodiments, electrical insulator tube 260 may be manufactured from a material having a thermal conductivity of less than 0.25 watts per meter kelvin or greater than 0.60 watts per meter kelvin.

Illustratively, first electrical insulator sleeve 210 may comprise a first electrical insulator sleeve distal end 211, a first electrical insulator sleeve proximal end 212, a first electrical insulator sleeve posterior offset 213, a first electrical insulator sleeve medial offset 214, and a first electrical insulator sleeve anterior offset 215. In one or more embodiments, first electrical insulator sleeve 210 may have dimensions configured for performing microsurgical procedures, e.g., first electrical insulator sleeve 210 may have an inner diameter larger than an outer diameter of first electrical conductor 230. Illustratively, first electrical insulator sleeve 210 may be configured to prevent an electrical connection between a portion of hypodermic tube 250 and a portion of first electrical conductor 230, e.g., first electrical insulator sleeve 210 may be configured to prevent an electrical current from flowing between a portion of hypodermic tube 250 and a portion of first electrical conductor 230. In one or more embodiments, first electrical insulator sleeve 210 may be configured to prevent an electrical connection between a portion of first electrical conductor 230 and a portion of second electrical conductor 240, e.g., first electrical insulator sleeve 210 may be configured to prevent an electrical current from flowing between a portion of first electrical conductor 230 and a portion of second electrical conductor 240. Illustratively, first electrical insulator sleeve 210 may be manufactured from any suitable material, e.g., polymers, metals, metal alloys, etc., or from any combination of suitable materials. In one or more embodiments, first electrical insulator sleeve 210 may be manufactured from a material having a dielectric strength in a range of 3500 to 4500 volts per mil, e.g., first electrical insulator sleeve 210 may be manufactured from a material having a dielectric strength of 4000 volts per mil. Illustratively, first electrical insulator sleeve 210 may be manufactured from a material having a dielectric strength of less than 3500 volts per mil or greater than 4500 volts per mil.

In one or more embodiments, second electrical insulator sleeve 220 may comprise a second electrical insulator sleeve distal end 221, a second electrical insulator sleeve proximal end 222, a second electrical insulator sleeve posterior offset 223, a second electrical insulator sleeve medial offset 224, and a second electrical insulator sleeve anterior offset 225. In one or more embodiments, second electrical insulator sleeve 220 may have dimensions configured for performing microsurgical procedures, e.g., second electrical insulator sleeve 220 may have an inner diameter larger than an outer diameter of second electrical conductor 240. Illustratively, second electrical insulator sleeve 220 may be configured to prevent an electrical connection between a portion of hypodermic tube 250 and a portion of second electrical conductor 240, e.g., second electrical insulator sleeve 220 may be configured to prevent an electrical current from flowing between a portion of hypodermic tube 250 and a portion of second electrical conductor 240. In one or more embodiments, second electrical insulator sleeve 220 may be configured to prevent an electrical connection between a portion of second electrical conductor 240 and a portion of second electrical conductor 230, e.g., second electrical insulator sleeve 220 may be configured to prevent an electrical current from flowing between a portion of second electrical conductor 240 and a portion of first electrical conductor 230. Illustratively, second electrical insulator sleeve 220 may be manufactured from any suitable material, e.g., polymers, metals, metal alloys, etc., or from any combination of suitable materials. In one or more embodiments, second electrical insulator sleeve 220 may be manufactured from a material having a dielectric strength in a range of 3500 to 4500 volts per mil, e.g., second electrical insulator sleeve 220 may be manufactured from a material having a dielectric strength of 4000 volts per mil. Illustratively, second electrical insulator sleeve 220 may be manufactured from a material having a dielectric strength of less than 3500 volts per mil or greater than 4500 volts per mil.

Figure 3A:
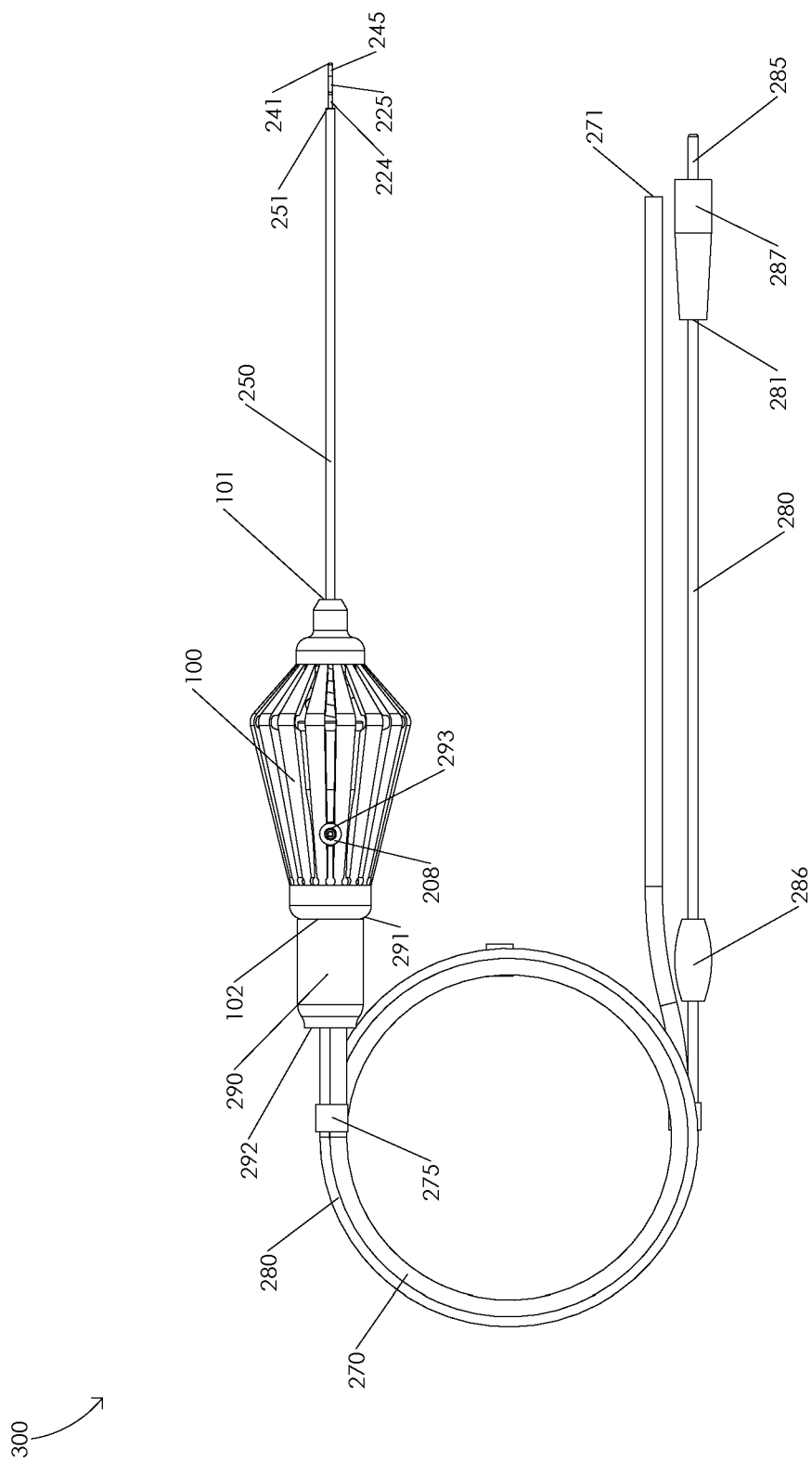
FIGS. 3A and 3B are schematic diagrams illustrating an assembled microsurgical bipolar forceps.
Figure 3B:
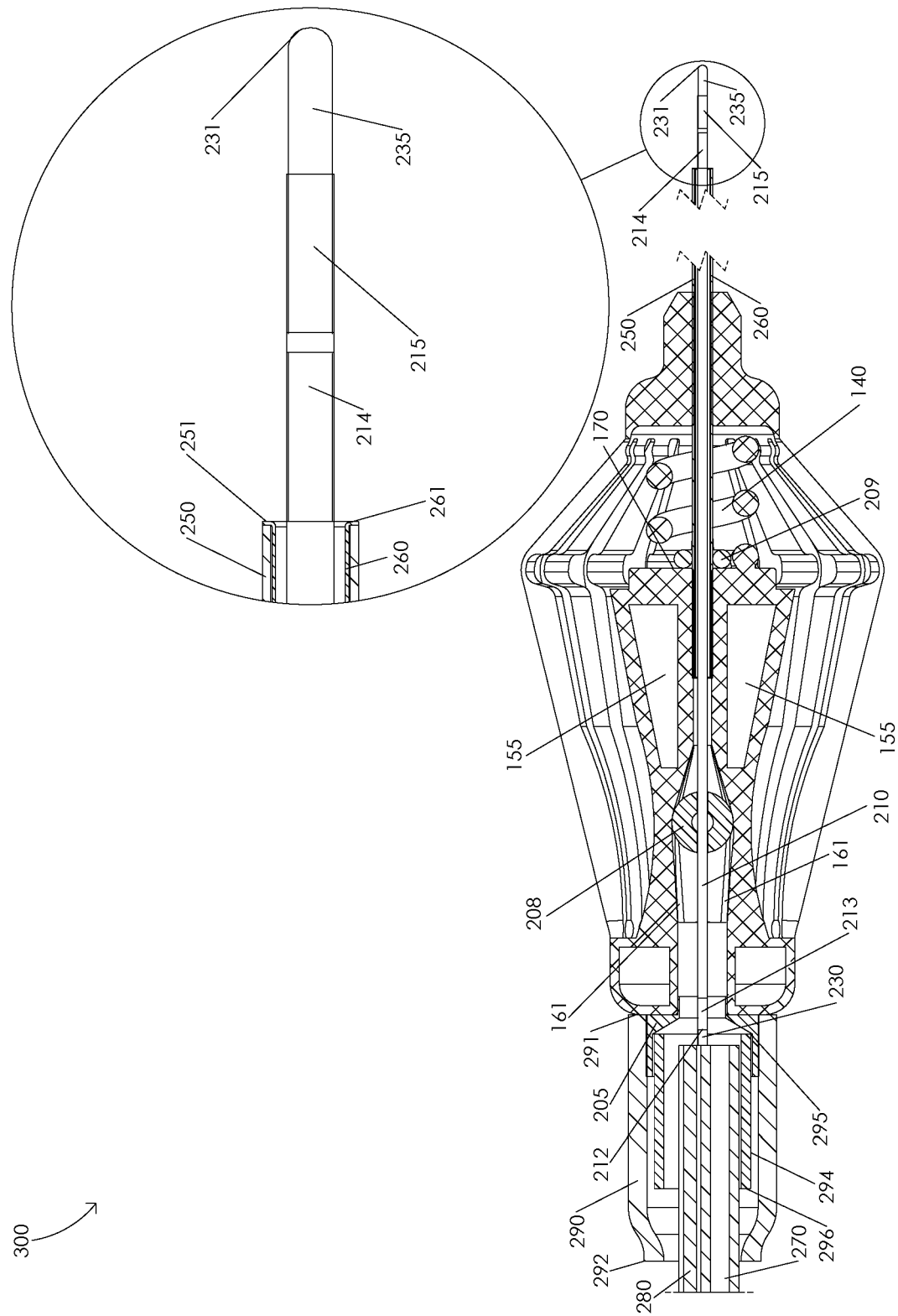

FIGS. 3A and 3B are schematic diagrams illustrating an assembled microsurgical bipolar forceps 300. FIG. 3A is a schematic diagram illustrating a side view of an assembled microsurgical bipolar forceps 300. FIG. 3B is a schematic diagram illustrating a cross-sectional view in a sagittal plane of an assembled microsurgical bipolar forceps 300. In one or more embodiments, electrical insulator tube 260 may be disposed in hypodermic tube 250, e.g., electrical insulator tube 260 may be disposed in hypodermic tube 250 wherein electrical insulator tube distal end 261 is adjacent to hypodermic tube distal end 251 and wherein electrical insulator tube proximal end 262 is adjacent to hypodermic tube proximal end 252. For example, electrical insulator tube distal end 261 may abut hypodermic tube distal end 251 and electrical insulator tube proximal end 262 may abut hypodermic tube proximal end 252.

Illustratively, electrical insulator tube 260 may be fixed in hypodermic tube 250, e.g., electrical insulator tube 260 may be fixed in hypodermic tube 250 by an adhesive, an epoxy, a friction fit, a weld, a tie, a crimp, etc. In one or more embodiments, a portion of hypodermic tube 250 may be disposed in a portion of handle 100, e.g., hypodermic tube proximal end 252 may be disposed in hypodermic tube housing 154. Illustratively, a portion of hypodermic tube 250 may be disposed in a portion of distal inner lumen 153, e.g., hypodermic tube proximal end 252 may be disposed in distal inner lumen 153. Illustratively, a portion of hypodermic tube 250 may be fixed in a portion of handle 100, e.g., a portion of hypodermic tube 250 may be fixed in a portion of handle 100 by an adhesive, an epoxy, a friction fit, a weld, a tie, a crimp, etc. In one or more embodiments, hypodermic tube 250 may be fixed in handle 100 wherein hypodermic tube distal end 251 extends out from handle distal end 100. Illustratively, hypodermic tube 250 may be disposed in handle 100 wherein a portion of hypodermic tube 250 is disposed in spring 140. In one or more embodiments, ring 209 may be disposed in a portion of handle 100, e.g., ring 209 may be disposed in a portion of handle 100 wherein ring 209 is adjacent to ring interface 170. For example, ring 209 may abut ring interface 170.

Illustratively, ring 209 may be fixed in a portion of handle 100, e.g., ring 209 may be fixed in a portion of handle 100 by an adhesive, an epoxy, a friction fit, a weld, a tie, a crimp, etc. In one or more embodiments, a portion of hypodermic tube 250 may be disposed in ring 209. Illustratively, ring 209 may be configured to form a hermetic seal around a portion of hypodermic tube 250, e.g., ring 209 may be configured to prevent an irrigation fluid from flowing around a portion of hypodermic tube 250. In one or more embodiments, hypodermic tube 250 may be disposed in handle 100 wherein hypodermic tube proximal end 252 is aligned with first irrigation fluid channel 161, e.g., hypodermic tube 250 may be disposed in handle 100 wherein an irrigation fluid flowing through first irrigation fluid channel 161 may be configured to flow into hypodermic tube 250 at hypodermic tube proximal end 252. Illustratively, hypodermic tube 250 may be disposed in handle 100 wherein hypodermic tube proximal end 252 is aligned with second irrigation fluid channel 162, e.g., hypodermic tube 250 may be disposed in handle 100 wherein an irrigation fluid flowing through second irrigation fluid channel 162 may be configured to flow into hypodermic tube 250 at hypodermic tube proximal end 252.

In one or more embodiments, first electrical conductor 230 may be disposed in first electrical insulator sleeve 210, e.g., first electrical insulator sleeve 210 may be disposed over a portion of first electrical conductor 230. Illustratively, first electrical conductor 230 may be disposed in first electrical insulator sleeve 210 wherein first electrical conductor distal end 231 extends out from first electrical insulator sleeve distal end 211. In one or more embodiments, first electrical conductor 230 may be disposed in first electrical insulator sleeve 210 wherein first electrical conductor proximal end 232 extends out from first electrical insulator sleeve proximal end 212. Illustratively, first electrical conductor 230 may be disposed in first electrical insulator sleeve 210 wherein first electrical conductor posterior offset 233 may be disposed in first electrical insulator sleeve posterior offset 213. In one or more embodiments, first electrical conductor 230 may be disposed in first electrical insulator sleeve 210 wherein first ramp 234 may be disposed in first electrical insulator sleeve medial offset 214. Illustratively, first electrical conductor 230 may be disposed in first electrical insulator sleeve 210 wherein first jaw 235 may be disposed in first electrical insulator sleeve anterior offset 215. In one or more embodiments, first electrical conductor 230 may be fixed in first electrical insulator sleeve 210, e.g., first electrical conductor 230 may be fixed in first electrical insulator sleeve 210 by an adhesive, an epoxy, a friction fit, a weld, a tie, a crimp, etc.

In one or more embodiments, second electrical conductor 240 may be disposed in second electrical insulator sleeve 220, e.g., second electrical insulator sleeve 220 may be disposed over a portion of second electrical conductor 240. Illustratively, second electrical conductor 240 may be disposed in second electrical insulator sleeve 220 wherein second electrical conductor distal end 241 extends out from second electrical insulator sleeve distal end 221. In one or more embodiments, second electrical conductor 240 may be disposed in second electrical insulator sleeve 220 wherein second electrical conductor proximal end 242 extends out from second electrical insulator sleeve proximal end 222. Illustratively, second electrical conductor 240 may be disposed in second electrical insulator sleeve 220 wherein second electrical conductor posterior offset 243 may be disposed in second electrical insulator sleeve posterior offset 223. In one or more embodiments, second electrical conductor 240 may be disposed in second electrical insulator sleeve 220 wherein second ramp 244 may be disposed in second electrical insulator sleeve medial offset 224. Illustratively, second electrical conductor 240 may be disposed in second electrical insulator sleeve 220 wherein second jaw 245 may be disposed in second electrical insulator sleeve anterior offset 225. In one or more embodiments, second electrical conductor 240 may be fixed in second electrical insulator sleeve 220, e.g., second electrical conductor 240 may be fixed in second electrical insulator sleeve 220 by an adhesive, an epoxy, a friction fit, a weld, a tie, a crimp, etc.

Illustratively, a portion of end plug 205 may be disposed in a portion of handle 100, e.g., end plug distal end 206 may be disposed in end plug housing 150. In one or more embodiments, end plug 205 may be disposed in handle 100 wherein a portion of end plug 205 extends out from handle proximal end 102, e.g., end plug 205 may be disposed in handle 100 wherein end plug proximal end 207 extends out from handle proximal end 102. Illustratively, a portion of end plug 205 may be fixed in a portion of handle 100, e.g., a portion of end plug 205 may be fixed in a portion of handle 100 by an adhesive, an epoxy, a friction fit, a weld, a tie, a crimp, etc. In one or more embodiments, a portion of inner sleeve 294 may be disposed in a portion of end plug 205, e.g., inner sleeve distal end 295 may be disposed in end plug proximal end 207. Illustratively, inner sleeve 294 may be disposed in end plug 205 wherein a portion of inner sleeve 294 extends out from end plug 205, e.g., inner sleeve 294 may be disposed in end plug 205 wherein inner sleeve proximal end 296 extends out from end plug proximal end 207. In one or more embodiments, a portion of inner sleeve 294 may be fixed in a portion of end plug 205, e.g., a portion of inner sleeve 294 may be fixed in a portion of end plug 205 by an adhesive, an epoxy, a friction fit, a weld, a tie, a crimp, etc. Illustratively, outer sleeve 290 may be disposed over a portion of end plug 250, e.g., a portion of end plug 250 may be disposed in outer sleeve 290. In one or more embodiments, end plug proximal end 207 may be disposed in outer sleeve 290, e.g., end plug proximal end 207 may be disposed in outer sleeve distal end 291. Illustratively, a portion of end plug 205 may be fixed in a portion of outer sleeve 290, e.g., a portion of end plug 205 may be fixed in a portion of outer sleeve 290 by an adhesive, an epoxy, a friction fit, a weld, a tie, a crimp, etc. In one or more embodiments, outer sleeve 290 may be disposed over a portion of inner sleeve 294, e.g., inner sleeve 294 may be disposed in outer sleeve 290. Illustratively, inner sleeve 294 may be completely disposed in outer sleeve 290, e.g., inner sleeve 294 may be disposed in outer sleeve 290 wherein inner sleeve distal end 295 is disposed between outer sleeve distal end 291 and outer sleeve proximal end 292 and wherein inner sleeve proximal end 296 is disposed between outer sleeve distal end 291 and outer sleeve proximal end 292. In one or more embodiments, outer sleeve 290 may be disposed over inner sleeve 294 wherein outer sleeve distal end 291 is adjacent to handle proximal end 102, e.g., outer sleeve 290 may be disposed over inner sleeve 294 wherein outer sleeve distal end 291 abuts handle proximal end 102. Illustratively, inner sleeve 294 may be fixed in outer sleeve 290, e.g., inner sleeve 294 may be fixed in outer sleeve 290 by an adhesive, an epoxy, a friction fit, a weld, a tie, a crimp, etc.

In one or more embodiments, a portion of irrigation tube 270 may be disposed in a portion of handle 100, e.g., irrigation tube proximal end 272 may be disposed in a portion of handle 100. Illustratively, a portion of irrigation tube 270 may be fixed in a portion of handle 100, e.g., a portion of irrigation tube 270 may be fixed in a portion of handle 100 by an adhesive, an epoxy, a friction fit, a weld, a tie, a crimp, etc. In one or more embodiments, a portion of irrigation tube 270 may be disposed in outer sleeve 290, inner sleeve 294, end plug 205, and handle 100. Illustratively, a portion of irrigation tube 270 may be fixed in outer sleeve 290, inner sleeve 294, end plug 205, and handle 100, e.g., a portion of irrigation tube 270 may be fixed in outer sleeve 290, inner sleeve 294, end plug 205, and handle 100 by an adhesive, an epoxy, a friction fit, a weld, a tie, a crimp, etc.

In one or more embodiments, irrigation tube 270 may be disposed in handle 100 wherein irrigation tube proximal end 272 is aligned with first irrigation fluid channel 161, e.g., irrigation tube 270 may be disposed in handle 100 wherein an irrigation fluid flowing through irrigation tube 270 may be configured to flow out from irrigation tube 270 at irrigation tube proximal end 272 and flow into first irrigation fluid channel 161. Illustratively, first irrigation fluid channel 161 may be configured to direct an irrigation fluid flowing out from irrigation tube proximal end 272 into hypodermic tube proximal end 152. In one or more embodiments, irrigation tube 270 may be disposed in handle 100 wherein irrigation tube proximal end 272 is aligned with second irrigation fluid channel 162, e.g., irrigation tube 270 may be disposed in handle 100 wherein an irrigation fluid flowing through irrigation tube 270 may be configured to flow out from irrigation tube 270 at irrigation tube proximal end 272 and flow into second irrigation fluid channel 162. Illustratively, second irrigation fluid channel 162 may be configured to direct an irrigation fluid flowing out from irrigation tube proximal end 272 into hypodermic tube proximal end 152. In one or more embodiments, directing an irrigation fluid into hypodermic tube proximal end 272 may be configured to direct the irrigation fluid through hypodermic tube 250. Illustratively, directing an irrigation fluid through hypodermic tube 250 may be configured to direct the irrigation fluid out from hypodermic tube distal end 251. In one or more embodiments, irrigation tube distal end 271 may be configured to interface with an irrigation pump module, e.g., irrigation tube distal end 271 may be configured to interface with an irrigation pump module of an electrosurgical generator. Illustratively, an irrigation pump module may be configured to pump an irrigation fluid into irrigation tube distal end 271. In one or more embodiments, an irrigation pump module may be configured to pump an irrigation fluid through irrigation tube 270. Illustratively, an irrigation pump module may be configured to pump an irrigation fluid out from irrigation tube proximal end 272. In one or more embodiments, an irrigation pump module may be configured to pump an irrigation fluid into first irrigation fluid channel 161. Illustratively, an irrigation pump module may be configured to pump an irrigation fluid through first irrigation fluid channel 161. In one or more embodiments, an irrigation pump module may be configured to pump an irrigation fluid out from first irrigation fluid channel 161. Illustratively, an irrigation pump module may be configured to pump an irrigation fluid into second irrigation fluid channel 162. In one or more embodiments, an irrigation pump module may be configured to pump an irrigation fluid through second irrigation fluid channel 162. Illustratively, an irrigation pump module may be configured to pump an irrigation fluid out from second irrigation fluid channel 162. In one or more embodiments, an irrigation pump module may be configured to pump an irrigation fluid into hypodermic tube proximal end 252. Illustratively, an irrigation pump module may be conic) figured to pump an irrigation fluid through hypodermic tube 250. In one or more embodiments, an irrigation pump module may be configured to pump an irrigation fluid out from hypodermic tube distal end 251.

In one or more embodiments, a portion of bipolar cord 280 may be disposed in a portion of handle 100, e.g., bipolar cord proximal end 282 may be disposed in a portion of handle 100. Illustratively, a portion of bipolar cord 280 may be fixed in a portion of handle 100, e.g., a portion of bipolar cord 280 may be fixed in a portion of handle 100 by an adhesive, an epoxy, a friction fit, a weld, a tie, a crimp, etc. In one or more embodiments, a portion of bipolar cord 280 may be disposed in outer sleeve 290, inner sleeve 294, end plug 205, and handle 100. Illustratively, a portion of bipolar cord 280 may be fixed in outer sleeve 290, inner sleeve 294, end plug 205, and handle 100, e.g., a portion of irrigation tube 270 may be fixed in outer sleeve 290, inner sleeve 294, end plug 205, and handle 100 by an adhesive, an epoxy, a friction fit, a weld, a tie, a crimp, etc.

In one or more embodiments, a portion of first electrical conductor 230 and a portion of first electrical insulator 210 may be disposed in hypodermic tube 250 wherein first electrical conductor distal end 231 extends out from hypodermic tube distal end 251, e.g., a portion of first electrical conductor 230 and a portion of first electrical insulator 210 may be disposed in electrical insulator tube 260 wherein first electrical conductor distal end 231 extends out from electrical insulator tube distal end 261. Illustratively, a portion of first electrical conductor 230 and a portion of first electrical insulator 210 may be disposed in hypodermic tube 250 wherein first electrical insulator distal end 211 extends out from hypodermic tube distal end 251, e.g., a portion of first electrical conductor 230 and a portion of first electrical insulator 210 may be disposed in electrical insulator tube 260 wherein first electrical insulator distal end 211 extends out from electrical insulator tube distal end 261. In one or more embodiments, a portion of first electrical conductor 230 and a portion of first electrical insulator 210 may be disposed in hypodermic tube 250 wherein first electrical conductor proximal end 232 extends out from hypodermic tube proximal end 252, e.g., a portion of first electrical conductor 230 and a portion of first electrical insulator 210 may be disposed in electrical insulator tube 260 wherein first electrical conductor proximal end 232 extends out from electrical insulator tube proximal end 262. Illustratively, a portion of first electrical conductor 230 and a portion of first electrical insulator 210 may be disposed in hypodermic tube 250 wherein first electrical insulator proximal end 212 extends out from hypodermic tube proximal end 252, e.g., a portion of first electrical conductor 230 and a portion of first electrical insulator 210 may be disposed in electrical insulator tube 260 wherein first electrical insulator proximal end 212 extends out from electrical insulator tube proximal end 262. In one or more embodiments, a portion of first electrical conductor 230 and a portion of first electrical insulator 210 may be disposed in handle 100 wherein first electrical conductor proximal end 232 extends out from handle proximal end 102. Illustratively, a portion of first electrical conductor 230 and a portion of first electrical insulator 210 may be disposed in handle 100 wherein first electrical insulator proximal end 212 extends out from handle proximal end 102. In one or more embodiments, a portion of first electrical conductor 230 and a portion of first electrical insulator 210 may be disposed in hypodermic tube housing 154, spring 140, distal inner lumen 153, proximal inner lumen 152, and end plug housing 150. Illustratively, a portion of first electrical conductor 230 and a portion of first electrical insulator 210 may be disposed in end plug 205. In one or more embodiments, a portion of first electrical conductor 230 and a portion of first electrical insulator 210 may be disposed in inner sleeve 294. Illustratively, first electrical conductor proximal end 232 may be disposed in inner sleeve 294. In one or more embodiments, first electrical insulator proximal end 212 may be disposed in inner sleeve 294. Illustratively, a portion of first electrical conductor 230 may be configured to interface with a portion of bipolar cord 280, e.g., a portion of first electrical conductor 230 may be configured to interface with bipolar cord proximal end 282. In one or more embodiments, first electrical conductor 230 may be electrically connected to bipolar cord 180, e.g., first electrical conductor 230 may be electrically connected to bipolar cord 180 in inner sleeve 294.

In one or more embodiments, a portion of second electrical conductor 240 and a portion of second electrical insulator 220 may be disposed in hypodermic tube 250 wherein second electrical conductor distal end 241 extends out from hypodermic tube distal end 251, e.g., a portion of second electrical conductor 240 and a portion of second electrical insulator 220 may be disposed in electrical insulator tube 260 wherein second electrical conductor distal end 241 extends out from electrical insulator tube distal end 261. Illustratively, a portion of second electrical conductor 240 and a portion of second electrical insulator 220 may be disposed in hypodermic tube 250 wherein second electrical insulator distal end 221 extends out from hypodermic tube distal end 251, e.g., a portion of second electrical conductor 240 and a portion of second electrical insulator 220 may be disposed in electrical insulator tube 260 wherein second electrical insulator distal end 221 extends out from electrical insulator tube distal end 261. In one or more embodiments, a portion of second electrical conductor 240 and a portion of second electrical insulator 220 may be disposed in hypodermic tube 250 wherein second electrical conductor proximal end 242 extends out from hypodermic tube proximal end 252, e.g., a portion of second electrical conductor 240 and a portion of second electrical insulator 220 may be disposed in electrical insulator tube 260 wherein second electrical conductor proximal end 242 extends out from electrical insulator tube proximal end 262. Illustratively, a portion of second electrical conductor 240 and a portion of second electrical insulator 220 may be disposed in hypodermic tube 250 wherein second electrical insulator proximal end 222 extends out from hypodermic tube proximal end 252, e.g., a portion of second electrical conductor 240 and a portion of second electrical insulator 220 may be disposed in electrical insulator tube 260 wherein second electrical insulator proximal end 222 extends out from electrical insulator tube proximal end 262. In one or more embodiments, a portion of second electrical conductor 240 and a portion of second electrical insulator 220 may be disposed in handle 100 wherein second electrical conductor proximal end 242 extends out from handle proximal end 102. Illustratively, a portion of second electrical conductor 240 and a portion of second electrical insulator 220 may be disposed in handle 100 wherein second electrical insulator proximal end 222 extends out from handle proximal end 102. In one or more embodiments, a portion of second electrical conductor 240 and a portion of second electrical insulator 220 may be disposed in hypodermic tube housing 154, spring 140, distal inner lumen 153, proximal inner lumen 152, and end plug housing 150. Illustratively, a portion of second electrical conductor 240 and a portion of second electrical insulator 220 may be disposed in end plug 205. In one or more embodiments, a portion of second electrical conductor 240 and a portion of second electrical insulator 220 may be disposed in inner sleeve 294. Illustratively, second electrical conductor proximal end 242 may be disposed in inner sleeve 294. In one or more embodiments, second electrical insulator proximal end 222 may be disposed in inner sleeve 294. Illustratively, a portion of second electrical conductor 240 may be configured to interface with a portion of bipolar cord 280, e.g., a portion of second electrical conductor 240 may be configured to interface with bipolar cord proximal end 282. In one or more embodiments, second electrical conductor 240 may be electrically connected to bipolar cord 180, e.g., second electrical conductor 240 may be electrically connected to bipolar cord 180 in inner sleeve 294.

Illustratively, first jaw 235 may be configured to prevent tissue from sticking to first jaw 235. In one or more embodiments, first jaw 235 may comprise an evenly polished material configured to prevent tissue sticking. Illustratively, first jaw 235 may be polished and then subjected to a surface treatment process configured to prevent tissue sticking, e.g., first jaw 235 may be coated by a material configured to prevent tissue sticking. In one or more embodiments, first jaw 235 may be subjected to a chemical surface treatment process configured to prevent tissue sticking. Illustratively, first jaw 235 may be subjected to a plasma surface treatment process configured to prevent tissue sticking. In one or more embodiments, first jaw 235 may be subjected to a particle deposition surface treatment process configured to prevent tissue sticking. Illustratively, first jaw 235 may be subjected to a vapor deposition surface treatment process configured to prevent tissue sticking. In one or more embodiments, first jaw 235 may be subjected to a surface treatment process configured to increase a contact angle between water and a surface of first jaw 235, e.g., first jaw 235 may be subjected to a surface treatment process configured to increase a hydrophobicity of a surface of first jaw 235 to prevent tissue sticking. Illustratively, first jaw 235 may be modified wherein a contact angle between a water droplet and a surface of first jaw 235 is in a range of 130.0 to 175.0 degrees, e.g., first jaw 235 may be modified wherein a contact angle between a water droplet and a surface of first jaw 235 is 165.0 degrees.

In one or more embodiments, first jaw 235 may be modified wherein a contact angle between a water droplet and a surface of first jaw 235 is less than 130.0 degrees or greater than 175.0 degrees. Illustratively, first jaw 235 may be subjected to a surface treatment process configured to decrease a contact angle between water and a surface of first jaw 235, e.g., first jaw 235 may be subjected to a surface treatment process configured to increase a hydrophilicity of a surface of first jaw 235 to prevent tissue sticking. In one or more embodiments, first jaw 235 may be modified wherein a contact angle between a water droplet and a surface of first jaw 235 is in a range of 5.0 to 40.0 degrees, e.g., first jaw 235 may be modified wherein a contact angle between a water droplet and a surface of first jaw 235 is 25.0 degrees. Illustratively, first jaw 235 may be modified wherein a contact angle between a water droplet and a surface of first jaw 235 is less than 5.0 degrees or greater than 40.0 degrees.

In one or more embodiments, a surface of first jaw 235 may have a roughness average in a range of 25.0 to 150.0 nanometers, e.g., a surface of first jaw 235 may have a roughness average of 98.8 nanometers. Illustratively, a surface of first jaw 235 may have a roughness average of less than 25.0 nanometers or greater than 150.0 nanometers. In one or more embodiments, a surface of first jaw 235 may have a root mean square average between height deviations over a total surface area of first jaw 235 in a range of 30.0 to 150.0 nanometers, e.g., a surface of first jaw 235 may have a root mean square average between height deviations over a total surface area of first jaw 235 of 112.0 nanometers. Illustratively, a surface of first jaw 235 may have a root mean square average between height deviations over a total surface area of first jaw 235 of less than 30.0 nanometers or greater than 150.0 nanometers. In one or more embodiments, a surface of first jaw 235 may have an average maximum profile of the ten greatest peak-to-valley separations over a total surface area of first jaw 235 in a range of 100.0 to 850.0 nanometers, e.g., a surface of first jaw 235 may have an average maximum profile of the ten greatest peak-to-valley separations over a total surface area of first jaw 235 of 435.0 nanometers. Illustratively, a surface of first jaw 235 may have an average maximum profile of the ten greatest peak-to-valley separations over a total surface area of first jaw 235 of less than 100.0 nanometers or greater than 850.0 nanometers. In one or more embodiments, a surface of first jaw 235 may have a maximum height difference between a highest point and a lowest point of a total surface area of first jaw 235 in a range of 200.0 to 1300.0 nanometers, e.g., a surface of first jaw 235 may have a maximum height difference between a highest point and a lowest point of a total surface area of first jaw 235 of 650.0 nanometers. Illustratively, a surface of first jaw 235 may have a maximum height difference between a highest point and a lowest point of a total surface area of first jaw 235 of less than 200.0 nanometers or greater than 1300.0 nanometers.

In one or more embodiments, first jaw 235 may be immersed in a chemical configured to produce a chrome conversion coating on first jaw 235 to prevent tissue from sticking to first jaw 235 during a surgical procedure. For example, first jaw 235 may comprise a chromate conversion coating configured to prevent tissue from sticking to first jaw 235 during a surgical procedure. Illustratively, first jaw 235 may be immersed in a phosphoric acid based cleaner and then immersed in a chromic acid based coating chemical to produce a chrome conversion coating on first jaw 235. In one or more embodiments, first jaw 235 may be polished to a mirror finish, and then immersed in a phosphoric acid based cleaner, and then immersed in a chromic acid based coating chemical to produce a chrome conversion coating on first jaw 235. Illustratively, first jaw 235 may be immersed in, e.g., Iridite, Alodine, etc., to produce a chrome conversion coating on first jaw 235 configured to prevent tissue from sticking to first jaw 235 during a surgical procedure. In one or more embodiments, first jaw 235 may comprise a chrome conversion coating configured to increase an electrical conductivity of first jaw 235. Illustratively, first jaw 235 may comprise a chrome conversion coating configured to reduce thermal spread to non-target tissue during a surgical procedure.

Illustratively, second jaw 245 may be configured to prevent tissue from sticking to second jaw 245. In one or more embodiments, second jaw 245 may comprise an evenly polished material configured to prevent tissue sticking. Illustratively, second jaw 245 may be polished and then subjected to a surface treatment process configured to prevent tissue sticking, e.g., second jaw 245 may be coated by a material configured to prevent tissue sticking. In one or more embodiments, second jaw 245 may be subjected to a chemical surface treatment process configured to prevent tissue sticking. Illustratively, second jaw 245 may be subjected to a plasma surface treatment process configured to prevent tissue sticking. In one or more embodiments, second jaw 245 may be subjected to a particle deposition surface treatment process configured to prevent tissue sticking. Illustratively, second jaw 245 may be subjected to a vapor deposition surface treatment process configured to prevent tissue sticking. In one or more embodiments, second jaw 245 may be subjected to a surface treatment process configured to increase a contact angle between water and a surface of second jaw 245, e.g., second jaw 245 may be subjected to a surface treatment process configured to increase a hydrophobicity of a surface of second jaw 245 to prevent tissue sticking. Illustratively, second jaw 245 may be modified wherein a contact angle between a water droplet and a surface of second jaw 245 is in a range of 130.0 to 175.0 degrees, e.g., second jaw 245 may be modified wherein a contact angle between a water droplet and a surface of second jaw 245 is 165.0 degrees.

In one or more embodiments, second jaw 245 may be modified wherein a contact angle between a water droplet and a surface of second jaw 245 is less than 130.0 degrees or greater than 175.0 degrees. Illustratively, second jaw 245 may be subjected to a surface treatment process configured to decrease a contact angle between water and a surface of second jaw 245, e.g., second jaw 245 may be subjected to a surface treatment process configured to increase a hydrophilicity of a surface of second jaw 245 to prevent tissue sticking. In one or more embodiments, second jaw 245 may be modified wherein a contact angle between a water droplet and a surface of second jaw 245 is in a range of 5.0 to 40.0 degrees, e.g., second jaw 245 may be modified wherein a contact angle between a water droplet and a surface of second jaw 245 is 25.0 degrees. Illustratively, second jaw 245 may be modified wherein a contact angle between a water droplet and a surface of second jaw 245 is less than 5.0 degrees or greater than 40.0 degrees.

In one or more embodiments, a surface of second jaw 245 may have a roughness average in a range of 25.0 to 150.0 nanometers, e.g., a surface of second jaw 245 may have a roughness average of 98.8 nanometers. Illustratively, a surface of second jaw 245 may have a roughness average of less than 25.0 nanometers or greater than 150.0 nanometers. In one or more embodiments, a surface of second jaw 245 may have a root mean square average between height deviations over a total surface area of second jaw 245 in a range of 30.0 to 150.0 nanometers, e.g., a surface of second jaw 245 may have a root mean square average between height deviations over a total surface area of second jaw 245 of 112.0 nanometers. Illustratively, a surface of second jaw 245 may have a root mean square average between height deviations over a total surface area of second jaw 245 of less than 30.0 nanometers or greater than 150.0 nanometers. In one or more embodiments, a surface of second jaw 245 may have an average maximum profile of the ten greatest peak-to-valley separations over a total surface area of second jaw 245 in a range of 100.0 to 850.0 nanometers, e.g., a surface of second jaw 245 may have an average maximum profile of the ten greatest peak-to-valley separations over a total surface area of second jaw 245 of 435.0 nanometers. Illustratively, a surface of second jaw 245 may have an average maximum profile of the ten greatest peak-to-valley separations over a total surface area of second jaw 245 of less than 100.0 nanometers or greater than 850.0 nanometers. In one or more embodiments, a surface of second jaw 245 may have a maximum height difference between a highest point and a lowest point of a total surface area of second jaw 245 in a range of 200.0 to 1300.0 nanometers, e.g., a surface of second jaw 245 may have a maximum height difference between a highest point and a lowest point of a total surface area of second jaw 245 of 650.0 nanometers. Illustratively, a surface of second jaw 245 may have a maximum height difference between a highest point and a lowest point of a total surface area of second jaw 245 of less than 200.0 nanometers or greater than 1300.0 nanometers.

In one or more embodiments, second jaw 245 may be immersed in a chemical configured to produce a chrome conversion coating on second jaw 245 to prevent tissue from sticking to second jaw 245 during a surgical procedure. For example, second jaw 245 may comprise a chromate conversion coating configured to prevent tissue from sticking to second jaw 245 during a surgical procedure. Illustratively, second jaw 245 may be immersed in a phosphoric acid based cleaner and then immersed in a chromic acid based coating chemical to produce a chrome conversion coating on second jaw 245. In one or more embodiments, second jaw 245 may be polished to a mirror finish, and then immersed in a phosphoric acid based cleaner, and then immersed in a chromic acid based coating chemical to produce a chrome conversion coating on second jaw 245. Illustratively, second jaw 245 may be immersed in, e.g., Iridite, Alodine, etc., to produce a chrome conversion coating on second jaw 245 configured to prevent tissue from sticking to second jaw 245 during a surgical procedure. In one or more embodiments, second jaw 245 may comprise a chrome conversion coating configured to increase an electrical conductivity of second jaw 245. Illustratively, second jaw 245 may comprise a chrome conversion coating configured to reduce thermal spread to non-target tissue during a surgical procedure.

Illustratively, an electrosurgical generator may be configured to apply an electric potential difference between first jaw 235 and second jaw 245, e.g., an electrosurgical generator may be configured to apply a voltage between first jaw 235 and second jaw 245. In one or more embodiments, an electrosurgical generator may be configured to cause an electrical current to flow out from the electrosurgical generator, through bipolar cord 180, through first electrical conductor 230, through a tissue, through second electrical conductor 240, through bipolar cord 180, and into the electrical surgical generator. Illustratively, an electrosurgical generator may be configured to cause an electrical current to flow out from the electrosurgical generator, through bipolar cord 180, through second electrical conductor 240, through a tissue, through first electrical conductor 230, through bipolar cord 180, and into the electrical surgical generator. In one or more embodiments, causing a current to flow through a tissue may be configured to increase a temperature of first jaw 235 and second jaw 245. Illustratively, increasing a temperature of first jaw 235 and second jaw 245 may be configured to cauterize a tissue.

Illustratively, coagulating a tissue, cauterizing a tissue, ablating a tissue, sealing a vessel, or inducing hemostasis may be configured to increase a temperature of first jaw 235. In one or more embodiments, increasing a temperature of first jaw 235 may facilitate thermal spread to non-target tissue, e.g., increasing a temperature of first jaw 235 may facilitate thermal spread to healthy tissue. Illustratively, an irrigation fluid may ingress irrigation tube 270 at irrigation tube distal end 271. In one or more embodiments, an irrigation fluid may egress irrigation tube 270 at irrigation tube proximal end 272. Illustratively, an irrigation fluid may ingress first irrigation fluid channel 161, flow through first irrigation fluid channel 161, and egress first irrigation fluid channel 161. In one or more embodiments, an irrigation fluid may ingress second irrigation fluid channel 162, flow through second irrigation fluid channel 162, and egress second irrigation fluid channel 162. Illustratively, an irrigation fluid may ingress hypodermic tube 250 at hypodermic tube proximal end 252. In one or more embodiments, an irrigation fluid may egress hypodermic tube 250 at hypodermic tube distal end 251. Illustratively, an egress of an irrigation fluid out from hypodermic tube distal end 251 may be configured to decrease a temperature of first jaw 235. Illustratively, decreasing a temperature of first jaw 235 may be configured to prevent thermal spread to a non-target tissue, e.g., decreasing a temperature of first jaw 235 may be configured to prevent thermal spread to healthy tissue. In one or more embodiments, coagulating a tissue, cauterizing a tissue, ablating a tissue, sealing a vessel, or inducing hemostasis may cause tissue to stick to first jaw 235. Illustratively, an egress of an irrigation fluid out from hypodermic tube distal end 251 may be configured to prevent tissue from sticking to first jaw 235.

Illustratively, coagulating a tissue, cauterizing a tissue, ablating a tissue, sealing a vessel, or inducing hemostasis may be configured to increase a temperature of second jaw 245. In one or more embodiments, increasing a temperature of second jaw 245 may facilitate thermal spread to non-target tissue, e.g., increasing a temperature of second jaw 245 may facilitate thermal spread to healthy tissue. Illustratively, an irrigation fluid may ingress irrigation tube 270 at irrigation tube distal end 271. In one or more embodiments, an irrigation fluid may egress irrigation tube 270 at irrigation tube proximal end 272. Illustratively, an irrigation fluid may ingress first irrigation fluid channel 161, flow through first irrigation fluid channel 161, and egress first irrigation fluid channel 161. In one or more embodiments, an irrigation fluid may ingress second irrigation fluid channel 162, flow through second irrigation fluid channel 162, and egress second irrigation fluid channel 162. Illustratively, an irrigation fluid may ingress hypodermic tube 250 at hypodermic tube proximal end 252. In one or more embodiments, an irrigation fluid may egress hypodermic tube 250 at hypodermic tube distal end 251. Illustratively, an egress of an irrigation fluid out from hypodermic tube distal end 251 may be configured to decrease a temperature of second jaw 245. Illustratively, decreasing a temperature of second jaw 245 may be configured to prevent thermal spread to a non-target tissue, e.g., decreasing a temperature of second jaw 245 may be configured to prevent thermal spread to healthy tissue. In one or more embodiments, coagulating a tissue, cauterizing a tissue, ablating a tissue, sealing a vessel, or inducing hemostasis may cause tissue to stick to second jaw 245. Illustratively, an egress of an irrigation fluid out from hypodermic tube distal end 251 may be configured to prevent tissue from sticking to second jaw 245.

Figure 4A:
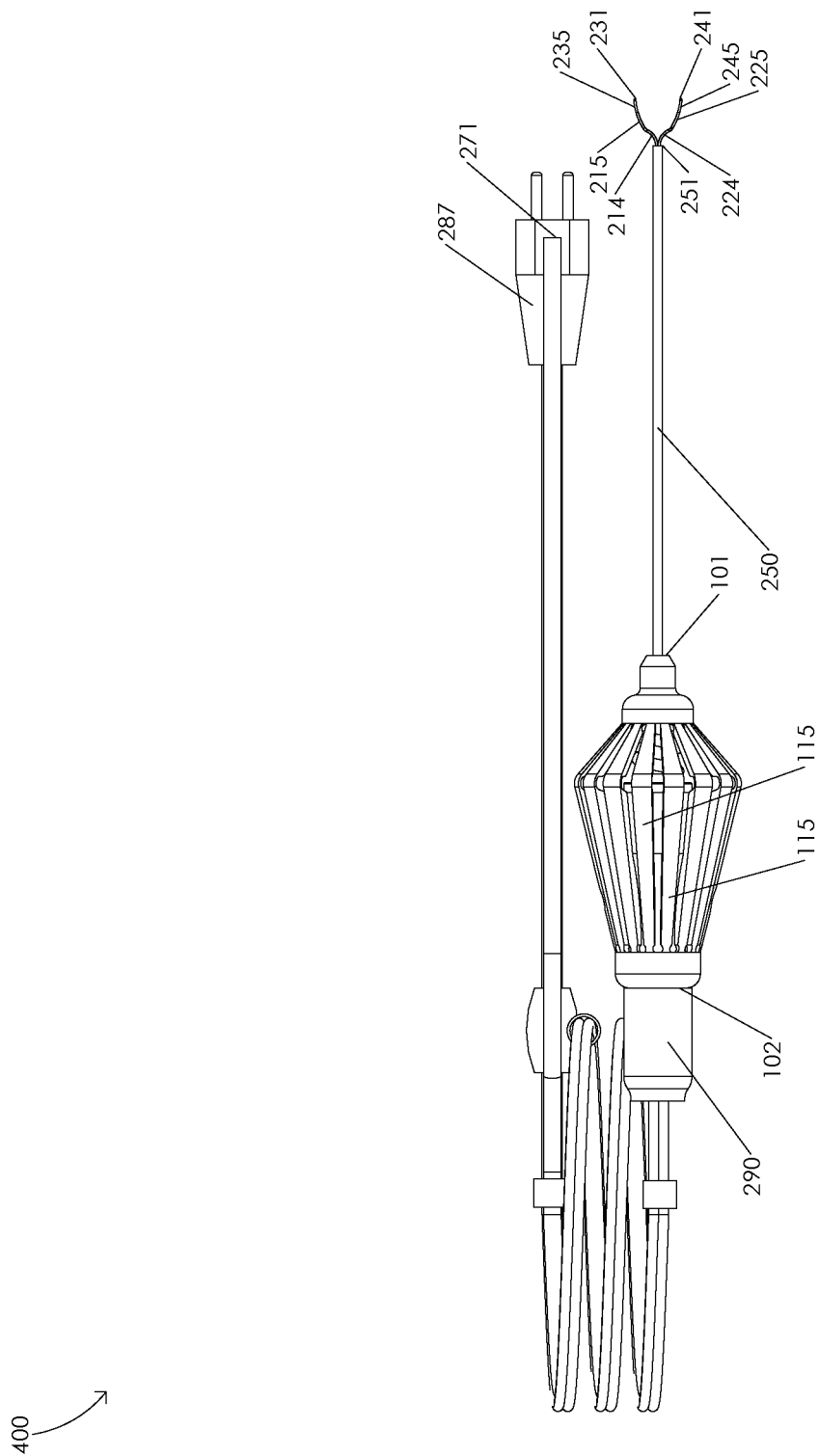
FIGS. 4A, 4B, and 4C are schematic diagrams illustrating a closing of an assembled microsurgical bipolar forceps jaws.
Figure 4B:
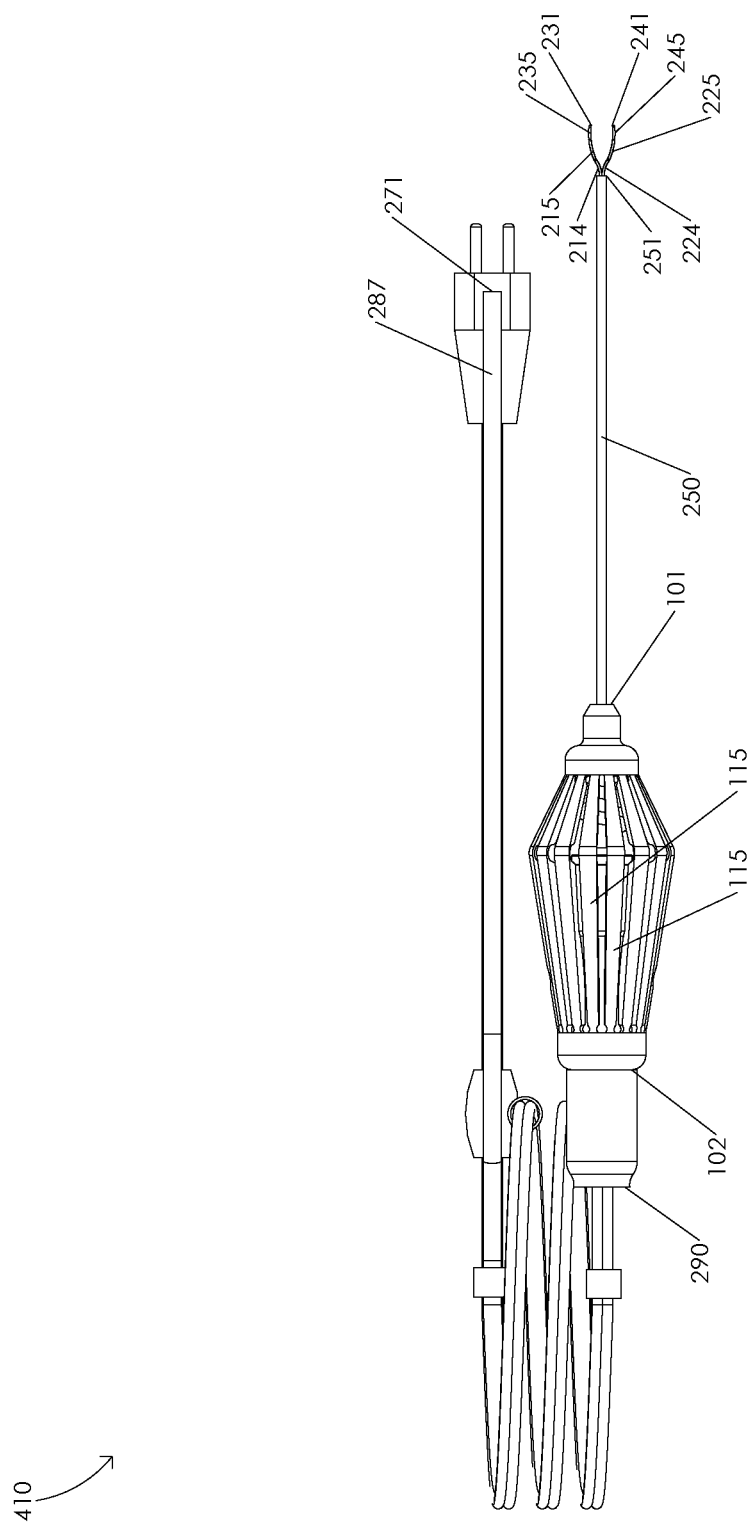
Figure 4C:
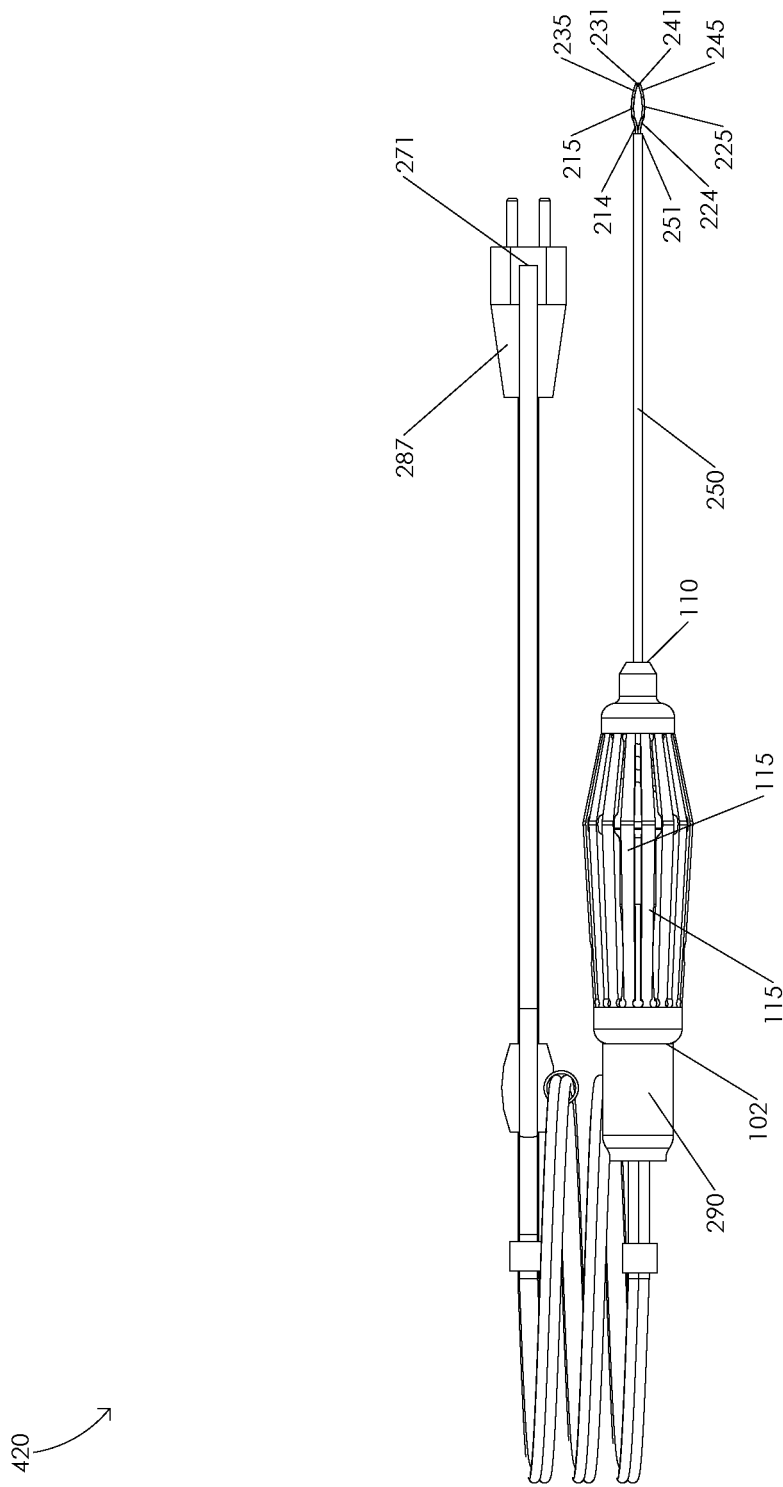

FIGS. 4A, 4B, and 4C are schematic diagrams illustrating a closing of an assembled microsurgical bipolar forceps jaws. FIG. 4A is a schematic diagram illustrating a top view of an open microsurgical bipolar forceps 400. In one or more embodiments, first jaw 235 and second jaw 245 may be separated when assembled microsurgical bipolar forceps 300 comprises an open microsurgical bipolar forceps 400. FIG. 4B is a schematic diagram illustrating a top view of a partially closed microsurgical bipolar forceps 410. Illustratively, a compression of actuation structure 110 may be configured to extend hypodermic tube 250 relative to first electrical conductor 230 and second electrical conductor 240. In one or more embodiments, a compression of actuation structure 110 may be configured to extend a portion of hypodermic tube 250 over a portion of first electrical conductor 230 and a portion of second electrical conductor 240, e.g., a compression of actuation structure 110 may be configured to extend hypodermic tube distal end 251 over is first ramp 234 and second ramp 244. Illustratively, an extension of hypodermic tube distal end 251 over first ramp 234 and second ramp 244 may be configured to decrease a distance between first jaw 235 and second jaw 245. In one or more embodiments, a surgeon may dispose a tissue between first jaw 235 and second jaw 245 to cauterize the tissue. FIG. 4C is a schematic diagram illustrating a top view of a closed microsurgical bipolar forceps 420. Illustratively, a compression of actuation structure 110 may be configured to cause contact between first jaw 235 and second jaw 245, e.g., a compression of actuation structure 110 may be configured to cause a contact between first electrical conductor distal end 231 and second electrical conductor distal end 241. In one or more embodiments, first jaw 235 and second jaw 245 may be in contact when assembled microsurgical bipolar forceps 300 comprises a closed microsurgical bipolar forceps 420.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of a bipolar forceps, the teachings of the present invention are equally suitable to any systems where the functionality may be employed. Therefore, it is the object of the appended claims to cover all such variations and modifications as come within the true spirit and scope of the invention.

What is claimed is:

1. An electrosurgical instrument comprising:
   a handle having a handle distal end and a handle proximal end;
   an actuation structure of the handle having an actuation structure distal end and an actuation structure proximal end;
   a plurality of actuation limbs of the actuation structure;
   a hypodermic tube having a hypodermic tube distal end and a hypodermic tube proximal end, the hypodermic tube disposed in the actuation structure wherein the hypodermic tube distal end extends out from the actuation structure distal end;
   a bipolar cord having a bipolar cord distal end and a bipolar cord proximal end;
   a first electrical conductor having a first electrical conductor distal end and a first electrical conductor proximal end, the first electrical conductor disposed in the hypodermic tube and the actuation structure wherein the first electrical conductor is electrically connected to the bipolar cord and wherein the first electrical conductor distal end extends out from the hypodermic tube distal end;
   a first ramp of the first electrical conductor;
   a first jaw of the first electrical conductor;
   a second electrical conductor having a second electrical conductor distal end and a second electrical conductor proximal end, the second electrical conductor disposed in the hypodermic tube and the actuation structure wherein the second electrical conductor is electrically connected to the bipolar cord and wherein the second electrical conductor distal end extends out from the hypodermic tube distal end;
   a second ramp of the second electrical conductor;
   a second jaw of the second electrical conductor; and
   a first electrical insulator sleeve having a first electrical insulator sleeve distal end, a first electrical insulator sleeve proximal end, a first electrical insulator sleeve medial off-set, and a first electrical insulator sleeve anterior offset, the first electrical insulator sleeve disposed over the first electrical conductor wherein the first electrical conductor distal end extends out from the first electrical insulator sleeve distal end, the first electrical conductor proximal end extends out from the first electrical insulator proximal end, the first ramp is disposed in the first electrical insulator sleeve medial offset, and a portion of the first jaw is disposed in the first electrical insulator sleeve anterior offset;
   wherein the hypodermic tube is configured for extension relative to the first electrical conductor and the second electrical conductor to move the first jaw and second jaw between an open position to a closed position.

2. The instrument of claim 1 further comprising: an electrical insulator tube having an electrical insulator tube distal end and an electrical insulator tube proximal end, the electrical insulator tube disposed in the hypo-dermic tube.

3. The instrument of claim 2 wherein the second electrical conductor is disposed in the electrical insulator tube.

4. The instrument of claim 3 wherein the first electrical conductor is disposed in the electrical insulator tube.

5. The instrument of claim 1 further comprising:
   a second electrical insulator sleeve having a second electrical insulator sleeve distal end, a second electrical insulator sleeve proximal end, a second electrical insulator sleeve medial offset, and a second electrical insulator sleeve anterior offset, the second electrical insulator sleeve disposed over the second electrical conductor wherein the second electrical conductor distal end extends out from the second electrical insulator sleeve distal end, the second electrical conductor proximal end extends out from the second electrical insulator proximal end, the second ramp is disposed in the second electrical insulator sleeve medial offset, and a portion of the second jaw is disposed in the second electrical insula-tor sleeve anterior offset.

6. The instrument of claim 1 further comprising: an irrigation tube having an irrigation tube distal end and an irrigation tube proximal end.

7. The instrument of claim 6 further comprising:
   an end plug having an end plug distal end and an end plug proximal end, the end plug disposed in a portion of the actuation structure wherein the irrigation tube is disposed in the end plug.

8. The instrument of claim 7 further comprising: a first irrigation fluid channel of the actuation structure.

9. The instrument of claim 8 further comprising: a second irrigation fluid channel of the actuation structure.

10. The instrument of claim 7 further comprising: an inner sleeve having an inner sleeve distal end and an inner sleeve proximal end wherein the inner sleeve distal end is disposed in the end plug.

11. The instrument of claim 10 further comprising: an outer sleeve having an outer sleeve distal end and an outer sleeve proximal end, the outer sleeve disposed over the inner sleeve.

12. The instrument of claim 1 further comprising: a spring in the handle.

13. The instrument of claim 1 further comprising: an end plug housing of the handle.

14. The instrument of claim 1 further comprising:
   a ring interface of the handle; and
   a ring disposed adjacent to the ring interface.

15. The instrument of claim 1 further comprising: a distal void of the handle.

16. The instrument of claim 15 further comprising: a proximal void of the handle.

17. The instrument of claim 1 further comprising: a wire lock housing of the handle.

18. The instrument of claim 1 further comprising: a distal inner lumen of the handle.

19. The instrument of claim 18 further comprising: a proximal inner lumen of the handle.

20. An electrosurgical instrument comprising:
a handle having a handle distal end and a handle proximal end;
an actuation structure of the handle having an actuation structure distal end and an actuation structure proximal end;
a hypodermic tube having a hypodermic tube distal end and a hypodermic tube proximal end, the hypodermic tube disposed in the actuation structure wherein the hypodermic tube distal end extends out from the actuation structure distal end;
a bipolar cord having a bipolar cord distal end and a bipolar cord proximal end;
a first electrical conductor having a first electrical conductor distal end and a first electrical conductor proximal end, the first electrical conductor disposed in the hypodermic tube and the actuation structure wherein the first electrical conductor is electrically connected to the bipolar cord and wherein the first electrical conductor distal end extends out from the hypodermic tube distal end;
a first jaw of the first electrical conductor;
a second electrical conductor having a second electrical conductor distal end and a second electrical conductor proximal end, the second electrical conductor disposed in the hypodermic tube and the actuation structure wherein the second electrical conductor is electrically connected to the bipolar cord and wherein the second electrical conductor distal end extends out from the hypodermic tube distal end;
a second jaw of the second electrical conductor; and
a first electrical insulator sleeve having a first electrical insulator sleeve distal end, a first electrical insulator sleeve proximal end, a first electrical insulator sleeve medial off-set, and a first electrical insulator sleeve anterior offset, the first electrical insulator sleeve disposed over the first electrical conductor wherein the first electrical conductor distal end extends out from the first electrical insulator sleeve distal end, the first electrical conductor proximal end extends out from the first electrical insulator proximal end, the first ramp is disposed in the first electrical insulator sleeve medial offset, and a portion of the first jaw is disposed in the first electrical insulator sleeve anterior offset;
wherein the actuation structure is configured to move the first jaw and second jaw between an open position to a closed position.

\* \* \* \* \*